(12) United States Patent
Hess et al.

(10) Patent No.: US 10,215,217 B2
(45) Date of Patent: Feb. 26, 2019

(54) LOCKING FASTENER WITH DEFLECTABLE LOCK

(71) Applicant: Enduralock, LLC

(72) Inventors: Harold Hess, Leawood, KS (US);
Tracy Hockenhull, Lenexa, KS (US);
Warren Moore, Lenexa, KS (US);
Armando Perez, III, Los Angeles, CA (US)

(73) Assignee: Enduralock, LLC, Overland Park, KS (US)

( * ) Notice: Subject to any disclaimer, the term of this patent is extended or adjusted under 35 U.S.C. 154(b) by 83 days.

(21) Appl. No.: 15/447,570

(22) Filed: Mar. 2, 2017

(65) Prior Publication Data
US 2017/0175795 A1 Jun. 22, 2017

Related U.S. Application Data

(63) Continuation-in-part of application No. 15/099,763, filed on Apr. 15, 2016, now Pat. No. 9,841,046.
(Continued)

(51) Int. Cl.
*F16B 39/24* (2006.01)
*F16B 37/00* (2006.01)
(Continued)

(52) U.S. Cl.
CPC .............. *F16B 39/24* (2013.01); *F16B 37/00* (2013.01); *F16B 39/282* (2013.01); *F16B 39/34* (2013.01); *F16B 43/00* (2013.01)

(58) Field of Classification Search
CPC .......... F16B 37/00; F16B 39/24; F16B 39/32; F16B 39/34; F16B 39/282; F16B 43/00
(Continued)

(56) References Cited

U.S. PATENT DOCUMENTS

| 687,774 A | 12/1901 | Oliver |
| 955,054 A | 4/1910 | Darby et al. |

(Continued)

FOREIGN PATENT DOCUMENTS

| CN | 105003518 A | 10/2015 |
| JP | 7217634 A | 8/1995 |

(Continued)

OTHER PUBLICATIONS

International Search Report and Written Opinion in International Application No. PCT/US2018/019328 dated May 8, 2018.
(Continued)

*Primary Examiner* — Roberta S Delisle
(74) *Attorney, Agent, or Firm* — Armstrong Teasdale LLP

(57) ABSTRACT

A locking mechanism for a fastener is provided. The locking mechanism includes a lock nut, a lock member, and a lock washer. The lock nut is releasably coupled to the lock nut for rotation therewith. The lock member includes an annular body having a radially-extending detent member. The lock washer includes an axially-extending wall about a periphery of the lock washer. The axially-extending wall defines an inner cavity for receiving a portion of the annular body of the lock member therein and includes comprising a plurality of radially-extending notches defined therein. The notches are configured to receive the radially-extending detent member.

20 Claims, 19 Drawing Sheets

Related U.S. Application Data

(60) Provisional application No. 62/148,846, filed on Apr. 17, 2015, provisional application No. 62/193,437, filed on Jul. 16, 2015.

(51) Int. Cl.
  *F16B 43/00* (2006.01)
  *F16B 39/34* (2006.01)
  *F16B 39/282* (2006.01)

(58) Field of Classification Search
  USPC .................................. 411/326, 329, 330, 331
  See application file for complete search history.

(56) References Cited

U.S. PATENT DOCUMENTS

| | | | |
|---|---|---|---|
| 961,371 A | 6/1910 | Posey | |
| 1,140,974 A | 5/1915 | Formby | |
| 1,142,345 A | 6/1915 | Major | |
| 1,225,626 A | 5/1917 | Hannon et al. | |
| 1,246,353 A | 11/1917 | Thigpen | |
| 1,249,336 A | 12/1917 | Cook | |
| 1,289,710 A | 12/1918 | Ervin | |
| 1,337,424 A | 4/1920 | Word | |
| 1,403,902 A | 1/1922 | Fields | |
| 1,526,914 A | 2/1925 | Kibler | |
| 1,651,188 A * | 11/1927 | Cole | F16B 39/32 411/204 |
| 2,018,574 A | 10/1935 | Richter | |
| 2,141,701 A | 12/1938 | Uherkovich | |
| 2,398,965 A | 4/1946 | Rounds | |
| 3,189,075 A | 6/1965 | Jobe | |
| 5,180,265 A * | 1/1993 | Wiese | F16B 39/08 411/150 |
| 5,190,423 A * | 3/1993 | Ewing | F16B 39/282 411/134 |
| 5,224,806 A | 7/1993 | Duran | |
| 5,314,279 A * | 5/1994 | Ewing | F16B 39/282 411/134 |
| 5,356,253 A * | 10/1994 | Whitesell | F16B 25/0021 411/188 |
| 5,460,468 A | 10/1995 | Distacio | |
| 5,538,378 A | 7/1996 | Van Der Drift | |
| 5,575,602 A | 11/1996 | Savage et al. | |
| 5,597,278 A * | 1/1997 | Peterkort | F16C 25/06 411/120 |
| 5,606,753 A * | 3/1997 | Hashimoto | F16B 39/32 411/120 |
| 5,618,143 A * | 4/1997 | Cronin, II | B25B 13/48 411/120 |
| 5,702,214 A | 12/1997 | Duran | |
| 5,713,708 A | 2/1998 | Van Derdrift et al. | |
| 5,735,853 A | 4/1998 | Olerud | |
| 5,951,224 A | 9/1999 | Distasio | |
| 6,010,289 A | 1/2000 | Distasio et al. | |
| 6,082,941 A | 7/2000 | Dupont et al. | |
| 6,139,550 A | 10/2000 | Michelson | |
| 6,258,089 B1 | 7/2001 | Campbell et al. | |
| 6,261,291 B1 | 7/2001 | Talaber et al. | |
| 6,361,257 B1 | 3/2002 | Grant | |
| 6,383,186 B1 | 5/2002 | Michelson | |
| 6,398,783 B1 | 6/2002 | Michelson | |
| 6,413,259 B1 | 7/2002 | Lyons et al. | |
| 6,434,792 B1 | 8/2002 | Williamson | |
| 6,554,555 B2 | 4/2003 | Imahigashi | |
| 6,602,255 B1 | 8/2003 | Campbell et al. | |
| 6,626,907 B2 | 9/2003 | Campbell et al. | |
| 6,695,846 B2 | 2/2004 | Richelsoph et al. | |
| 6,755,833 B1 | 6/2004 | Paul et al. | |
| 6,935,822 B2 | 8/2005 | Hartmann et al. | |
| 6,976,816 B2 * | 12/2005 | Slesinski | F16B 39/103 411/120 |
| 6,976,817 B1 | 12/2005 | Grainger | |
| 7,189,044 B2 | 3/2007 | Ball | |
| 7,270,509 B2 | 9/2007 | Disantis et al. | |
| 7,318,825 B2 | 1/2008 | Butler et al. | |
| 7,374,495 B2 | 5/2008 | Ball | |
| 7,621,943 B2 | 11/2009 | Michelson | |
| 7,763,056 B2 | 7/2010 | Dalton | |
| 7,857,839 B2 | 12/2010 | Duong et al. | |
| 7,887,547 B2 | 2/2011 | Campbell et al. | |
| 7,909,859 B2 | 3/2011 | Mosca et al. | |
| 7,955,037 B2 | 6/2011 | Disantis et al. | |
| 8,123,788 B2 | 2/2012 | Michelson | |
| 8,262,711 B2 | 9/2012 | Hess | |
| 8,292,373 B2 * | 10/2012 | Rieger | B60B 27/0005 301/105.1 |
| 8,366,365 B2 | 2/2013 | Disantis et al. | |
| 8,591,157 B1 * | 11/2013 | Stewart | F16B 31/028 411/10 |
| 2005/0207865 A1 | 9/2005 | Disantis et al. | |
| 2005/0209599 A1 | 9/2005 | Brunsvold | |
| 2006/0015104 A1 | 1/2006 | Dalton | |
| 2009/0060682 A1 | 3/2009 | Yeh et al. | |
| 2009/0192553 A1 | 7/2009 | Maguire et al. | |
| 2010/0121383 A1 | 5/2010 | Stanaford et al. | |
| 2011/0188970 A1 | 8/2011 | Dillon et al. | |
| 2012/0063864 A1 | 3/2012 | Hess | |
| 2014/0356097 A1 | 12/2014 | Hess et al. | |
| 2016/0084291 A1 | 3/2016 | Stewart | |
| 2016/0305465 A1 | 10/2016 | Hess et al. | |

FOREIGN PATENT DOCUMENTS

| | | |
|---|---|---|
| JP | H084743 A | 1/1996 |
| JP | 2008004743 A | 1/2008 |
| KR | 200241791 Y1 | 10/2001 |
| KR | 10863200 B1 | 10/2008 |
| KR | 2011099247 A | 9/2011 |

OTHER PUBLICATIONS

International Search Report and Written Opinion for PCT/US2016/027744, 32 pages, dated Jul. 15, 2016.
PCT International Search Report and Written Opinion dated Nov. 26, 2014 issued on corresponding PCT International Application No. PCT/US2014/051006.
International Preliminary Report (PCT/IB/373) and Written Opinion on Patentability (PCT/ISA/237) in corresponding International Application PCT/US2011/051189, dated Mar. 19, 2013.
TineLok: Overview, www.tinelok.com (2013).
TineLok, The Revolutionary Vibration-Proof Fastener System, www.tinelok.com (2013).
Written Opinion with International Search Report from Application No. PCT/US2011/051189, dated Jun. 28, 2012.

* cited by examiner

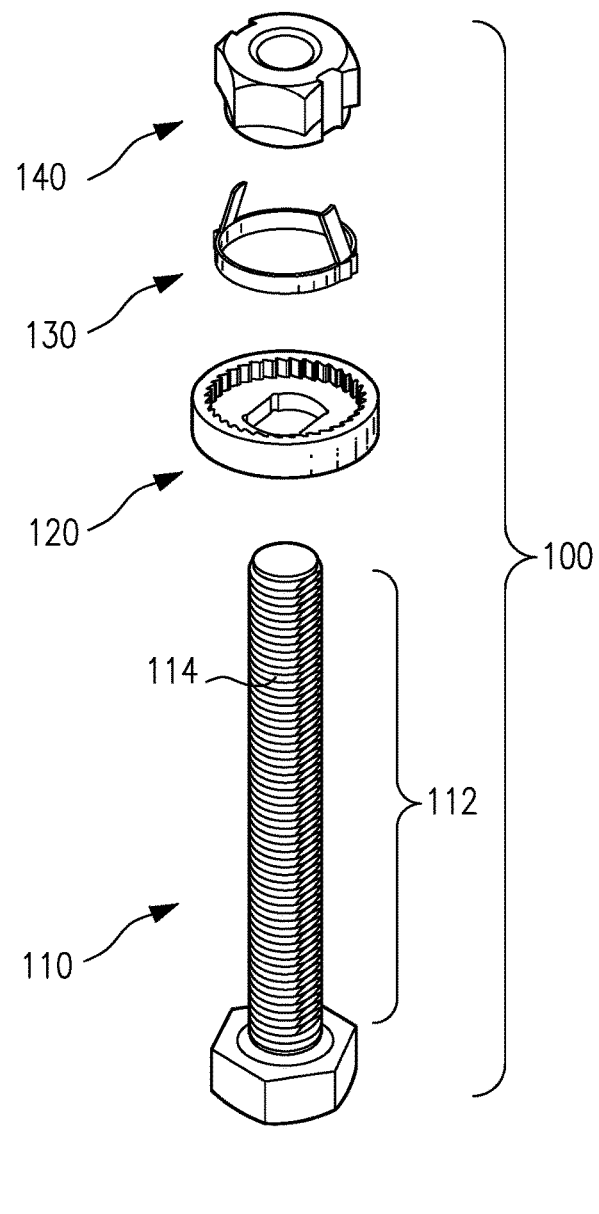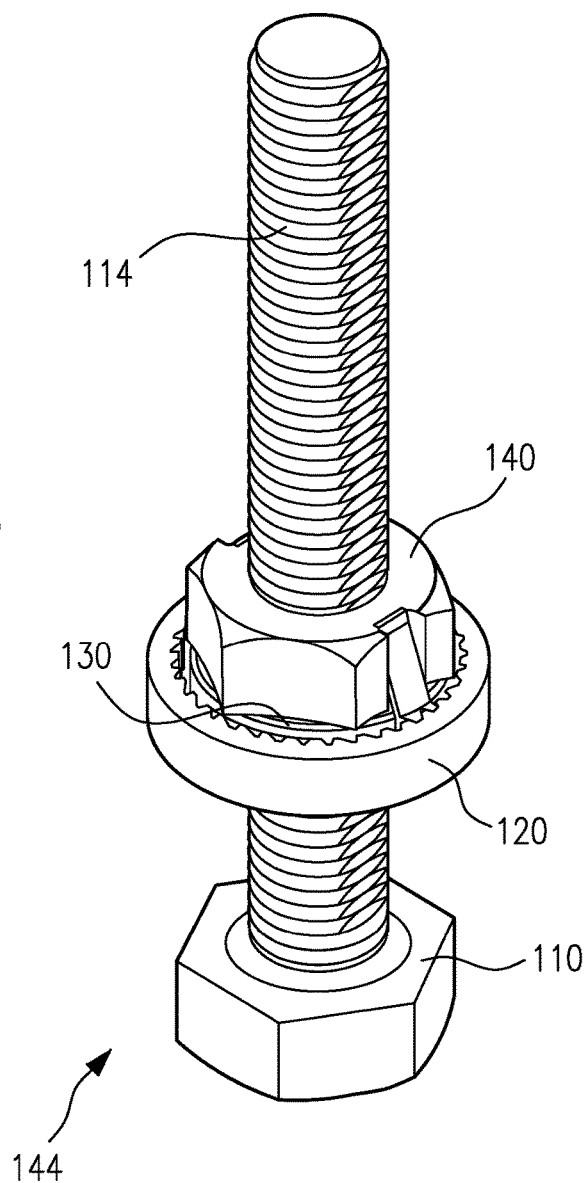
FIG. 1
FIG. 2

LOCKING FASTENER WITH DEFLECTABLE LOCK

CROSS REFERENCE TO RELATED APPLICATIONS

This application is a continuation-in-part application of U.S. patent application Ser. No. 15/099,763 filed Apr. 15, 2016, and claims priority to and the benefits of U.S. Provisional Patent Application Ser. No. 62/148,846 filed Apr. 17, 2015, and U.S. Provisional Patent Application Ser. No. 62/193,437 filed Jul. 16, 2015, each of which is hereby incorporated by reference in its entirety.

BACKGROUND

The field of the disclosure relates generally to fasteners, and more specifically to locking mechanisms for adjustable diameter threaded fasteners.

Fasteners commonly include mechanisms for ensuring that fastener elements do not loosen over time, potentially allowing joined elements to loosen or separate. Examples of mechanisms include thread bore inserts, and screw thread profiles that deform when tightened. Fasteners accessories like lock washers, cotter pins, and lock wires are also commonly used with fasteners to prevent fastener elements from loosening. Adhesive materials, like epoxy, can be applied to fastener threads to stake fastener elements to prevent fastener elements from loosening. Conventional fastener mechanisms, accessories, and adhesive materials may not be suitable for some applications, such as high temperature environments or with structures subject to vibration.

Such conventional mechanisms, accessories, and adhesive materials have generally been considered satisfactory for their intended purpose. However, there is still a need in the art for improved fasteners. The present disclosure provides a solution for this need.

BRIEF DESCRIPTION

In one aspect, a locking mechanism for a fastener is provided. The locking mechanism includes a lock nut. In addition, the locking mechanism includes a lock member releasably coupled to the lock nut for rotation therewith. The lock member includes an annular body having a radially-extending detent member. Moreover, the locking mechanism includes a lock washer having an axially-extending wall about a periphery of the lock washer. The axially-extending wall defines an inner cavity for receiving a portion of the annular body of the lock member therein. The axially-extending wall also includes a plurality of radially-extending notches defined therein configured to receive the radially-extending detent member.

In another aspect, an adjustable diameter fastener assembly is provided. The adjustable diameter fastener assembly includes a threaded member that defines a longitudinal axis and includes a body portion and at least one anti-rotation feature formed in the body portion. The adjustable diameter fastener assembly also includes a radially expandable bushing slidably coupled about the threaded member. Furthermore, the adjustable diameter fastener assembly includes a lock nut configured to threadably engage the threaded member. The lock nut includes a peripheral surface including an axially-extending slot defined therein. Moreover, the adjustable diameter fastener assembly includes a lock member releasably coupled to the lock nut. The lock member includes an annular body and an axially-extending spring finger coupled to the annular body. The axially-extending spring finger includes a free end that extends radially inward relative to the annular body. The annular body includes a radially-extending detent member. In addition, the adjustable diameter fastener assembly includes a lock washer including an axially-extending wall about a periphery of said lock washer. The axially-extending wall defines an inner cavity for receiving a portion of the annular body of the lock member therein and includes a plurality of radially-extending notches defined therein. Each radially-extending notch of the plurality of radially-extending notches is configured to receive the radially-extending detent member.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 1 is an exploded perspective view of a fastener device constructed in accordance with the present disclosure, showing a nut member, a lock member, a washer member, and a bolt member of the fastener device;

FIG. 2 is a perspective view of the fastener device of FIG. 1, showing the fastener device in an assembled configuration;

Figure 3:
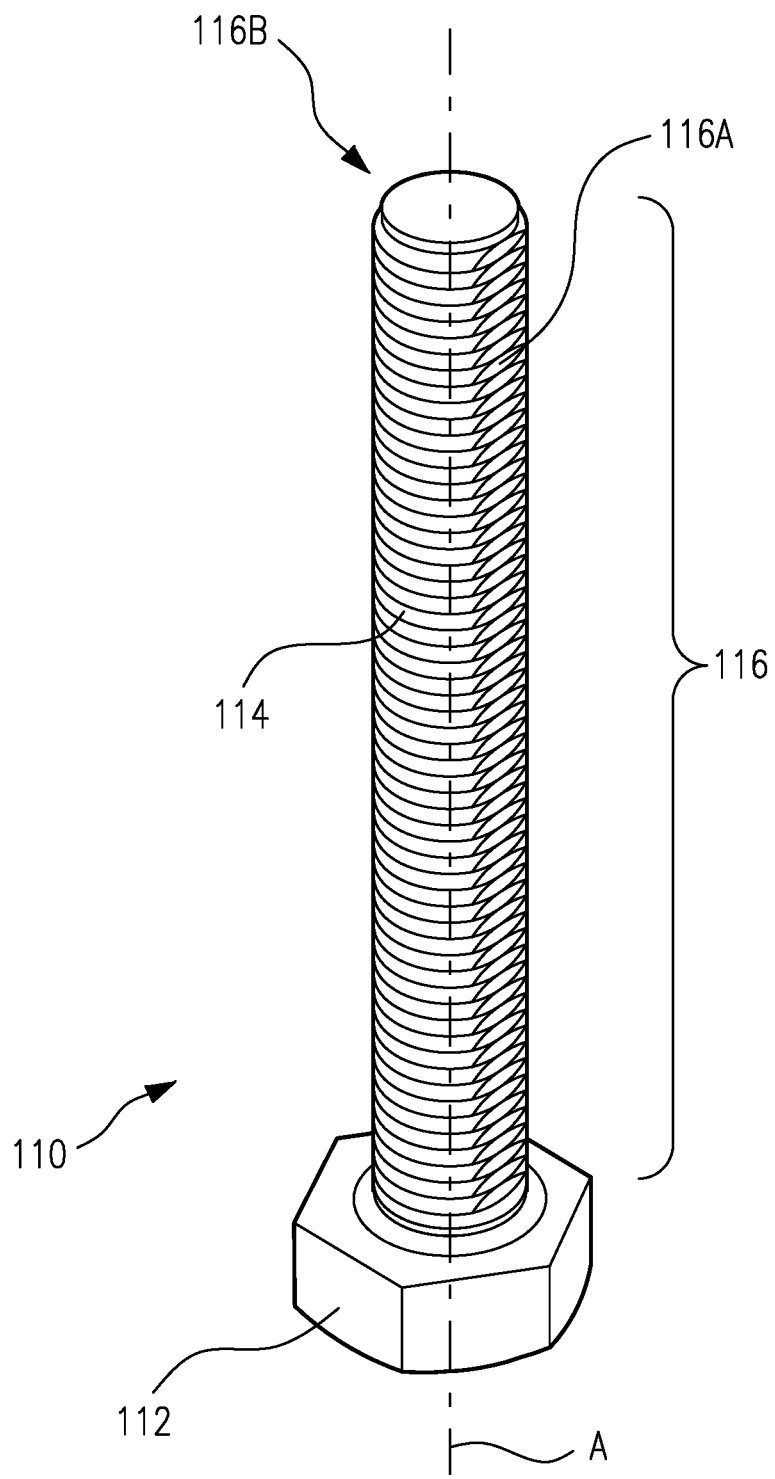
FIG. 3 is a perspective view of the bolt member of FIG. 1, showing the elongated body, threaded segment, and banking feature of the bolt member.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms such as "about," "approximately," and "substantially" are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

Relative descriptors used herein such as upward, downward, left, right, up, down, length, height, width, thickness, and the like are with reference to the figures, and not meant in a limiting sense. Additionally, the illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed fastener assemblies. Additionally, the shapes and sizes of components are also exemplary and can be altered without materially affecting or limiting the disclosed technology.

The subject invention is directed to a fastener locking mechanism including an elongated bolt member having a threaded segment with a banking feature, a washer member having a circumferential wall with radially inward facing engagement teeth and a banking portion that complements the banking feature of the bolt member, a lock member having an annular body with an upstanding spring finger and a tooth disposed on a radially outward surface of the annular body, and a nut member having a circumferential flat with an axial slot and a threaded bore corresponding to threaded segment of the bolt member. The banking feature of the bolt member cooperates with the banking portion of the washer member to fix the washer member in rotation relative to the bolt member. The spring finger of the lock member cooperates with the axial slot of the nut member to fix the lock member in rotation relative to the nut member. The tooth of the lock member is displaceable radially relative to the bolt member for engaging and disengaging the engagement teeth of the washer member. In a radially outer position, the tooth of the lock member intermeshes with the engagement teeth of the washer member to fix the lock member and nut member in rotation relative to the washer member. In a radially inner position, the tooth of the lock member is rotatable relative to the washer member such that the lock member and nut member are rotatable relative to the washer member and the bolt member.

In accordance with certain embodiments, the bolt member can include a flat. The flat can extend axially along a length of bolt member. The banking feature of the bolt member can include the flat. The flat can be radially adjacent to the threaded segment of the bolt member. The flat can be a first flat, and the bolt member can include one or more second flats. The banking feature can include both the first flat and the second flat. The second flat can extend axially along the bolt member. The second flat can be disposed on a side of the bolt member diametrically opposite the first flat. The threaded segment can extend circumferentially about the bolt member and couple the first flat with the second flat.

It is also contemplated that, in accordance with certain embodiments, the washer member can have opposed axial surfaces separated by an axial thickness of the washer member. A circumferential wall can extend from a periphery axially from a surface of washer member. Engagement teeth can be disposed on a radially inner surface of the circumferential wall. The engagement teeth can extend radially inward from the circumferential wall. A central aperture can extend through the thickness of the washer member between the axial surfaces of the washer member. The central aperture can include the banking portion that complements the banking feature of the bolt member. For example, one or more flat segments can bound the central aperture. The flat segment can correspond with the banking feature of the bolt member. The central aperture can include one or more arcuate segments bounding the central aperture. The arcuate segment can correspond to the threaded segment(s) of the bolt member. The central aperture can include both flat and arcuate segments, and a stress reduction feature can be disposed at an intersection of a flat segment and an arcuate segment.

In certain embodiments, the lock member can include a spring finger having a free end and a fixed end. The free end can be disposed radially inward of the fixed end. The fixed end can be connected to the annular body of the lock member. The tooth and the spring finger can be circumferentially aligned with one another. The annular body of the lock member can have a round, oval, square, rectangular, or any suitably shaped axial profile. The annular body can be deformable, for example becoming more round (or more elliptical) in response to inward force exerted on the spring finger at a location between the fixed and free ends of the spring finger. The spring finger can be a first spring finger, and the lock member can include a second spring finger connected to the annular body on a side of the annular body opposite the first spring finger.

In accordance with certain embodiments, the lock member can have a first and second teeth that each extend radially outward from the annular body of the lock member. The first and second teeth can be circumferentially adjacent to one another. The first and second teeth can also be circumferentially aligned to the spring tab. The first and second teeth can be disposed on opposite sides of the annular body of the lock member such that each extends radially in a direction opposite the other. The second tooth can be circumferentially aligned with a second spring finger of the lock member. It is also contemplated that more than one circumferentially adjacent tooth can be aligned to a first spring finger, and that more than one circumferentially adjacent tooth can be aligned to the second spring finger.

It is also contemplated that, in accordance with certain embodiments, the nut member can have an annular recess. The annular recess can have a diameter that is less than a diameter of the annular body of the lock member. The nut member can have a circumference with a plurality of faces. The plurality of faces of the nut member can form a hexagonal circumference extending about the nut member. One or more of the faces of the nut member can have an axial slot. The axial slot can extend between the annular recess and an end of the nut member opposite the annular recess of the nut member. It is contemplated that the nut member can have faces with axial slots disposed on faces that are diametrically opposed to one another.

In an aspect, the threaded segment and banking feature of the bolt member, central aperture and engagement teeth of the washer member, tooth and spring finger of the lock member, and axial slot of the nut member can cooperate as a locking mechanism. The locking mechanism can have a locked position wherein the annular body urges the lock member tooth radially outward such that the tooth intermeshes with the engagement teeth of the washer member, fixing the lock member in rotation relative to the washer member and preventing loosening of the nut member from the bolt member. The locking mechanism can have a tighten or release position wherein the annular body of the lock member urges the lock member tooth radially inward, rendering the lock member and nut member rotatable relative to the washer member and bolt member. It is contemplated that lock member can have a spring preload that normally urges the lock member tooth radially outward, and that a force exerted on the spring finger of the lock member can urge the lock member tooth radially inward to move to the reconfigure the locking mechanism from the locked position to the tighten or release position.

In another aspect, a spinal fixation system includes a fastener locking mechanism as described above and a rod. The rod seats in the bolt member and below the washer member. It is contemplated that tightening the nut member exerts force on the washer member which in turn urges the rod against the bolt member.

In certain embodiments, the bolt member can have a head portion coupled to an end of a stem section. The head portion can be fixed relative to the stem portion. A joint can be interposed between the head portion and the stem portion, the head portion thereby being movable relative to the stem portion. The head portion pivotable relative to the stem portion, such as in a conical movement envelope. The head portion can have a first threaded segment and the stem portion can have a second threaded segment. The first threaded segment can be a male threaded segment corresponding to a female threaded segment defined by the bore of the nut member. The second threaded segment can taper between an end adjacent to the head member and an end of the stem portion opposite the head portion. It is contemplated that the second threaded segment can have threads adapted for seating the bolt member to a bone structure, such as a pedicle.

In accordance with certain embodiments, the bolt member can include a tulip head. The tulip head can have a slot extending therethrough for seating the rod. The slot can be centrally disposed, extending across the top of the bolt member. The slot can be laterally disposed, extending across a side of the bolt member. Lobes can be defined on opposite sides of the slot. The lobes can have the banking feature of the bolt member defined thereon. The lobes can have the threaded segment of the bolt member defined thereon. In a contemplated exemplary embodiment, each lobe has portions of both the threaded segment and the banking feature defined thereon.

It is also contemplated that, in accordance with certain embodiments, the washer member can include a central bar portion. The central bar portion can extend across the washer member central aperture and divide the central aperture into first and second portions. One lobe of the bolt member tulip head can extend through the first portion of the central aperture, and the another lobe of the bolt member tulip head can extend through the second portion of the central aperture. The central bar portion can extend from the banking portion of the washer member such that, when the central bar portion is seated with the slot of the tulip head, the washer member is fixed in rotation relative to the tulip head. It is contemplated that central bar portion can seat slot of the tulip head, overlay the rod, and can be disposed between the nut member, lock member, and the stem of the bolt member.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

The present disclosure overcomes many of the prior art problems associated with threaded fasteners, including adjustable diameter fasteners. In general, threaded fasteners are used to fixedly connect two or more pieces in a variety of applications such as, without limitation, with surgical implants, industrial applications, aerospace applications, and building applications. Among other features and benefits, the disclosed fastening devices and systems can provide one or more of quick and easy installation and/or removal, vibration resistant secured tightness, and/or single end access for blind fastening applications. The advantages, and other features of the technology disclosed herein, will become more readily apparent to those having ordinary skill in the art from the following detailed description of certain preferred embodiments taken in conjunction with the drawings which set forth representative embodiments of the present disclosure and wherein like reference numerals identify similar structural elements.

FIG. 1 shows a fastener with a locking mechanism constructed in accordance with the present disclosure designated generally by reference numeral 100. Fastener device 100 generally includes an elongated bolt member 110, a washer member 120, a lock member 130, and a nut member 140. Bolt member 110 has a threaded segment 114. Threaded segment 114 includes male threads corresponding to female threads disposed on nut member 140. One or more of bolt member 110, washer member 120, lock member 130, and nut member 140 may include plastic, metal, a combination thereof, or any other suitable material.

With reference to FIG. 2, washer member 120 seats about threaded segment 114 such that washer member 120 is rotatably fixed and axially displaceable relative to bolt member 110. Lock member 130 seats about threaded segment 114 of bolt member 110 and against an axial face of washer member 120. Nut member 140 has female threads that thread engage male threads on threaded segment 114, and is disposed axially along bolt member 110 such that nut member 140 seats against washer member 120. Lock member 130 seats about threaded segment 114 and is axially interposed between washer member 120 and nut member 140.

With reference to FIG. 3, an exemplary bolt member 110 is shown. Bolt member 110 defines a fastener axis "A" and, in the illustrated exemplary embodiment, includes a head portion 112 disposed on an end opposite threaded segment 114. Threaded segment 114 has a banking feature 116 that, in the illustrated exemplary embodiment, includes a first longitudinally extending flat 116A and an opposed second longitudinally extending flat 116B. It is to be understood and appreciated that other banking feature geometries are possible within the scope of the present disclosure such as a single flat portion, notches, grooves, convex portions, concave portions, protrusions, slots, and/or combinations thereof. Examples of such features are shown and described in U.S. Patent Application Publication No. 2014/0308089 A1, the contents of which incorporated by reference herein in their entirely.

Figure 4:
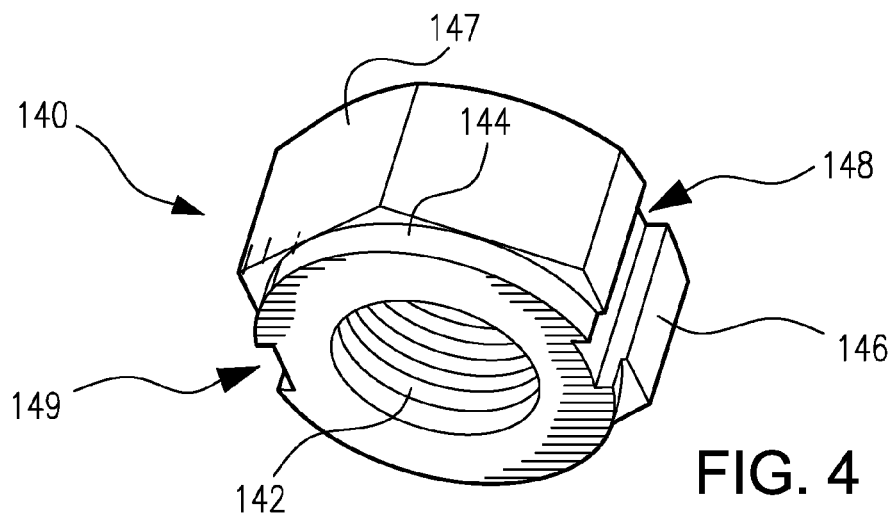
FIG. 4 is a perspective view of the nut member of FIG. 1, showing the threaded bore, annular recess, hexagonal recess, and an exemplary axial slot of the nut member.

With reference to FIG. 4, nut member 140 is shown. Nut member 140 includes a bore 142 having female threads, an annular recess 144, one or more slotted circumferential face 146, and one or more continuous face 147. Bore 142 extends between axially opposed faces of nut member 140. Annular recess 144 extends circumferentially about bore 142 and adjacent to the tool engagement faces of nut member 140. The one or more slotted circumferential face 146 and one or more continuous face 147 define tool engagement faces that extend axially between annular recess 144 and an axial face of nut member 140 that is opposite annular recess 144 and circumferentially about nut member 140. The tool engagement faces may correspond to one or more common tools, such as a wrench or socket, and in the illustrated exemplar embodiment define a hexagonal circumference. This allows for tightening or loosening nut member 140 using a common hand tool and without requiring use of a specialized tool.

The one or more slotted circumferential face 146 defines an axial slot 148. Axial slot 148 extends axially along slotted circumferential face 146 between annular recess 144 and the axial face of nut member 140 opposite annular recess 144, and has a circumferential width corresponding to the width of spring finger 134 (shown in FIG. 5) and spring finger 136 (shown in FIG. 5). This allows nut member 140 to cooperate with the preload of spring finger 134 such that, when axial slot 148 aligns in rotation about fastener axis "A" (shown in FIG. 3), spring finger 134 snaps into axial slot 148. As will be appreciated by those of skill in the art in view of the present disclosure, snapping spring finger 134 into axial slot 148 fixes lock member 130 in rotation relative to nut member 140.

In the illustrated exemplary embodiment shown in FIG. 4 axial slot 148 is a first axial slot and nut member 140 includes a second axial slot 149. Second axial slot 149 is disposed on a diametrically opposed side of nut member 140, i.e. on a side of axis "A" opposite first axial slot 148, and on a slotted face that is substantially parallel to slotted circumferential face 146. As will be appreciated by those of skill in the art in view of the present disclosure, nut member 140 can have one, two, or more than two axial slots. The number of axial slots on nut member 140 may correspond in number and circumferential position relative to those of lock member 130. Although two axial slots are shown in the illustrated exemplary embodiment, it is to be understood and appreciated that nut member 140 can have a single axial slot or more than two axial slots, as suitable for an intended application.

Figure 5:
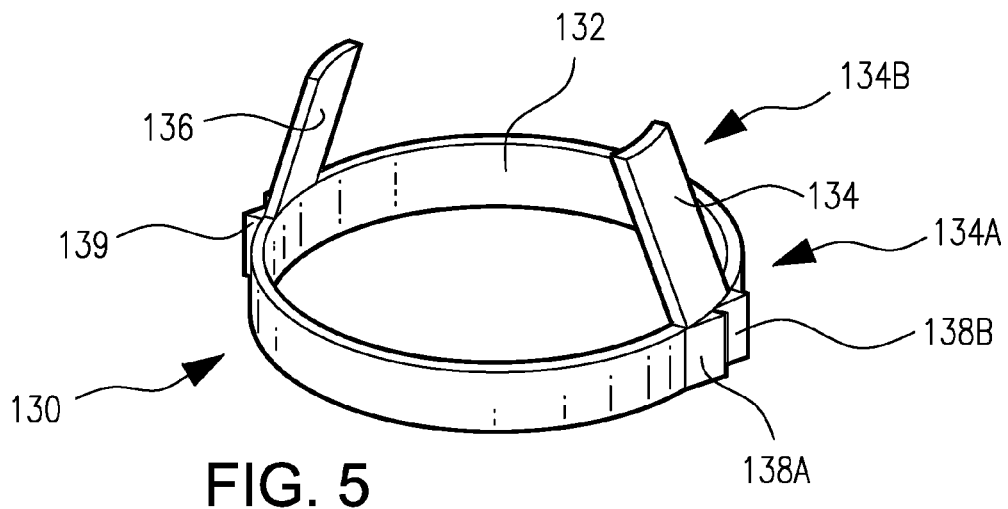
FIG. 5 is a perspective view of the lock member of FIG. 1, showing the deformable body, upstanding spring fingers, and teeth of the lock member.

With reference to FIG. 5, lock member 130 is shown. Lock member 130 includes a deformable annular body 132. In the illustrated exemplary embodiment annular body 132 has a ring-like shape. It is contemplated that annular body 132 may be round, oval, ellipsoid, or any other suitable shape, and is constructed from a resilient material, such as an elastomer or spring steel. Response to a radial force exerted thereon by one or more spring fingers 134, annular body 132 may become more or less round depending upon the amount of radial force exerted on annular body 132 and the spring constant of lock member 130.

Spring finger 134 upstands from annular body 132 and extends between a fixed end 134A and a free end 134B. Fixed end 134A connects to annular body 132. Spring finger 134 extends radially inward from fixed end 134A such that free end 134B is disposed radially inward of fixed end 134A. In the illustrated exemplary embodiment, spring finger 134 is a first spring finger and lock member 130 includes a second spring finger 136. Second spring finger 136 is similar to first spring tab 134, and is additionally connected to annular body 132 such that second spring finger 136 faces first spring finger 134 on a side of lock member 130 that is diametrically opposed to the first spring finger 134.

A tooth 138 is disposed on the radially outer surface of lock member 130 and is circumferentially aligned relative to spring finger 134. Tooth 138 includes a locking face 138B and a sliding face 138A that correspond to the locking faces and sliding faces of washer member 120 (shown in FIG. 4). This allows a tool, e.g. tool 10 (shown in FIG. 8), to slidably engage spring finger 134, thereby radially displacing tooth 138 relative to the engagement teeth 126 of washer member 120. In the illustrated exemplary embodiment, tooth 138 is one of a plurality of teeth, and a second tooth 139 is disposed on a diametrically opposite side of annular body 132 circumferentially adjacent to second spring finger 136. First tooth 138 and/or second tooth 139 can each be one of a plurality of circumferentially adjacent teeth arranged about the radially outer surface of annular body 132 for fixing lock member 130 in rotation relative to washer member 120 (shown in FIG. 6).

Figure 6:
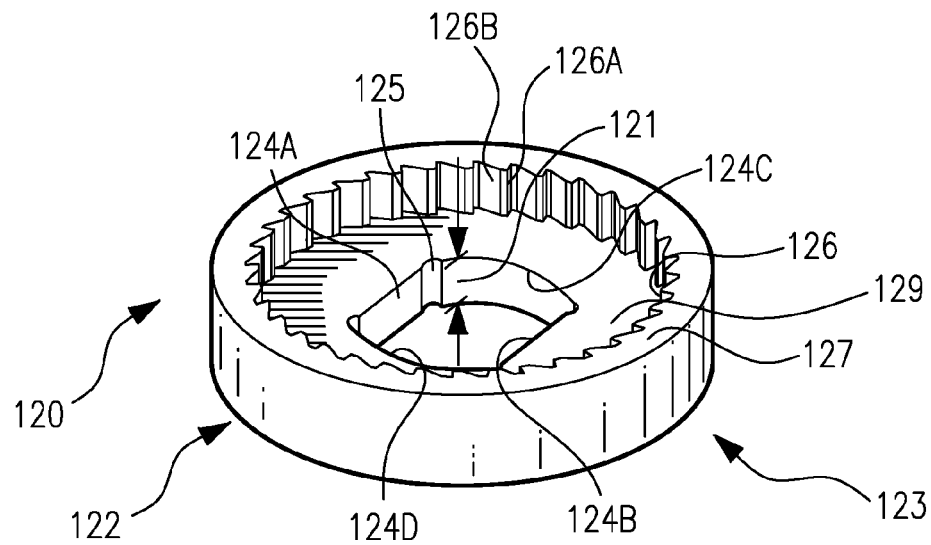
FIG. 6 is a perspective view of the washer member of FIG. 1, showing the washer member central aperture and banking portion, circumferential lip, and radial teeth oriented radially inwards relative to the circumferential lip.

With reference to FIG. 6, washer member 120 is shown. Washer member 120 has a central bore 121 that extends between a first axial face 129 and an opposed second axial face 123. First axial face 129 is separated from second axial face 123 by an axial thickness T of washer member 120. Central bore 121 is bounded by a plurality of banking segments that complement banking feature 116 of bolt member 110 (shown in FIG. 3). In the illustrated exemplary embodiment the plurality of banking segments includes pair of flats coupled by a pair of arcuate segments and a plurality of stress reduction features. In this respect central bore 121 includes a first flat 124A and a second flat 124B that bound central bore 121. A first arcuate segment 124C extends between first flat 124A and second flat 124B. A second arcuate segment 124D faces first arcuate segment 124C and extends between opposite ends first flat 124A and second flat 124B. Stress reduction features 125 are defined at corners of central bore 121 where respective flats and arcuate segments intersect one another. It will be appreciated that other banking segments are contemplated within the scope of the present disclosure.

A circumferential wall 127 extends axially from first axial face 129 about the periphery of washer member 120. Circumferential wall 127 has a plurality of engagement teeth 126. Engagement teeth 126 are distributed about a radially inner face of circumferential wall 127 and extend radially inward from circumferential wall 127 and towards central bore 121. In the illustrated exemplary embodiment, engagement teeth 126 include a locking face 126A that is substantially orthogonal with respect to circumferential wall 127 and a sliding face 126B that is oblique relative to circumferential wall 127.

Figure 7:
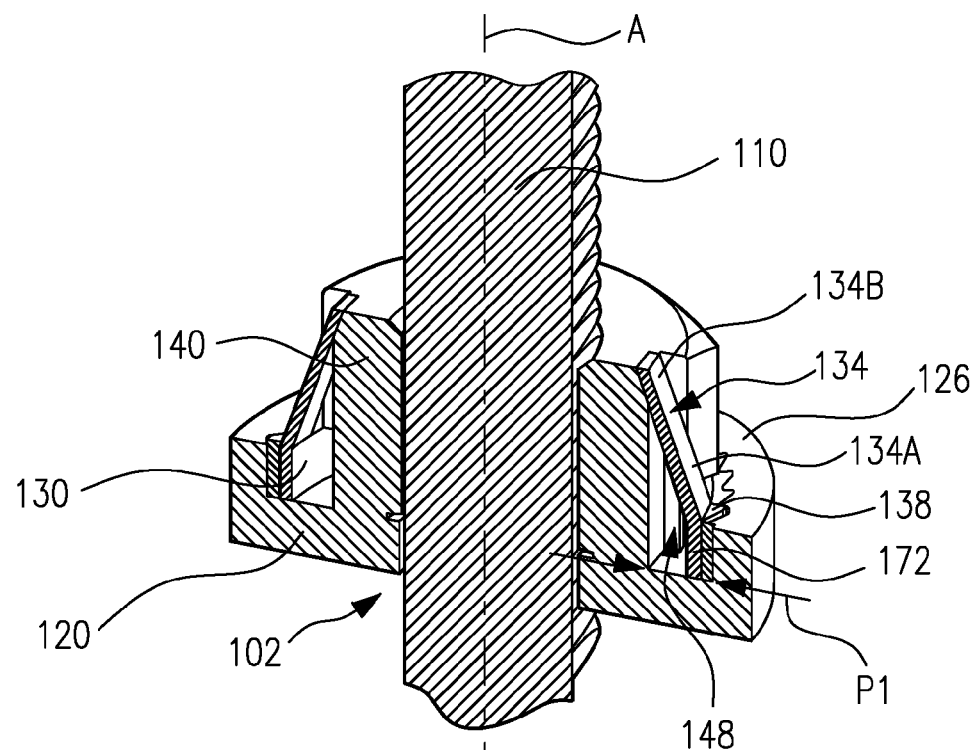
FIG. 7 is a perspective view of fastener of FIG. 1, showing the fastener and fastener locking mechanism in a locked position.
Figure 8:
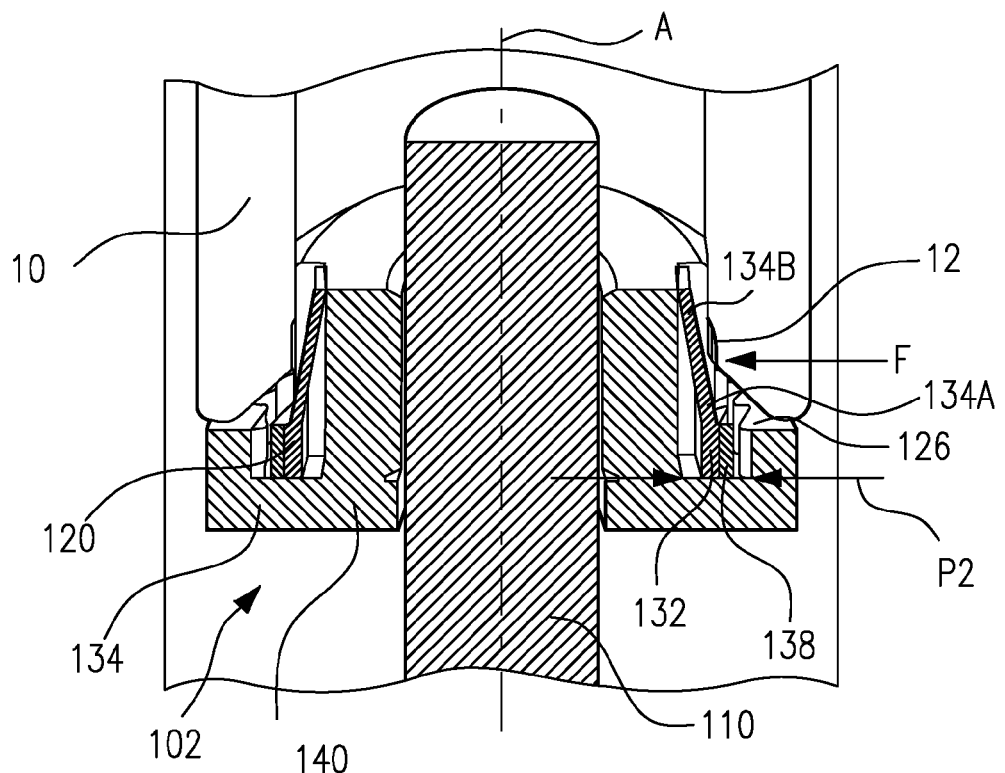
FIG. 8 is a perspective view of the fastener of FIG. 1, showing the fastener and fastener locking mechanism in a release or tighten position.

With reference to FIGS. 7 and 8, fastener 100 is shown in an assembled configuration. FIG. 7 shows fastener 100 with the locking mechanism 102 in a locked position. FIG. 8 shows fastener 100 with locking mechanism 102 in a tighten or release position. In the locked position shown in FIG. 7, washer member 120, lock member 130, and nut member 140 are each fixed both axially and in rotation relative to bolt member 110. In the tighten or release position shown in FIG. 8, lock member 130 and nut member 140 are both rotationally free relative to bolt member 110. As will be appreciated, rotation of nut member 140 relative to bolt member 110 displaces nut member 140 axially relative to bolt member 110, allowing corresponding axial displacement of washer member 120 and lock member 130 relative to bolt member 110.

As indicated in FIG. 7, fixed end 134A of spring finger 134 assumes a locked position radial offset P1 when locking mechanism 102 is in the locked position. At the locked position radial offset P1, deformable annular body 132 is urged radially outward at the circumferential position corresponding to spring finger 134. Urging annular body 132 radially outward at the location corresponding to spring finger 134 in turn urges tooth 138 of lock member 130 against engagement teeth 126 of washer member 120. Consequently, at circumferential arrangements where lock member tooth locking surface(s) 138A align and overlap in a coplanar arrangement with a corresponding locking surface 126A of engagement tooth 126, lock member 130 becomes rotational fixed relative to washer member 120.

As also indicated in FIG. 7, free end 134B of spring finger 134 seats within axial slot 148 when locking mechanism 102 is in the locked position. Seating free end 134B of spring finger 134 in axial slot 148 fixes lock member 130 in rotation with nut member 140. Fixing lock member 130 in rotation relative to nut member 140 causes lock member 130 to rotation with nut member 140. Consequently, when tooth 138 of lock member 130 seats against engagement teeth 126 of washer member 120, lock member 130 becomes fixed in rotation relative to washer member 120. As will be appreciated, since washer member 120 is fixed in rotation relative to both member the complementary banking member and banking portion of each, seating tooth 138 of lock member 130 against engagement tooth 126 also fixes nut member 140 in rotation relative to bolt member 110.

With reference to FIG. 8, fastener 100 is shown with locking mechanism 102 in the tighten or release position. Locking mechanism 102 moves from the locked position (shown in FIG. 7) to the illustrated tighten or release position by seating a tool over an end of fastener 100. In this respect tool 10 includes a finger contact surface 12 extending circumferentially about an interior recess of tool 10. Upon seating tool 10 seats over nut member 140 by axially displacing tool 10 relative to fastener 100, contact surface 12 comes into contact and exerts a contact force F on spring finger 134, oriented obliquely relative thereto, at a location between fixed end 134A and free end 134B of spring finger 134. Contact force F urges spring finger 134 radially inward relative to fastener axis "A," deforming annular body 132 such that fixed end 134A of spring finger 134 assumes an unlocked or tighten radial offset P2.

Unlocked or tighten radial offset P2 is smaller than locked radial offset P1. Moving fixed end 134A of spring finger 134 from locked radial offset P1 to unlocked or release radial offset P2 causes the locking face 138B of tooth 138 to slide across locking face of engagement tooth 126. This disengages tooth 138 of lock member 130 from engagement tooth 126 of washer member 120, allowing lock member 130 and nut member 140 to rotate relative to washer member 120 and bolt member 110. As will be appreciated, tool 10 may be rotated either clockwise or counterclockwise about fastener axis "A" to displace nut member 140 axially in either direction along fastener axis "A", tightening nut member 140 or loosening nut member 140 as appropriate. Thus, when a tool such as a conventional socket wrench is applied to nut member 140, lock member 130 is deflected radially inward such that teeth of lock member 130 disengage teeth of washer member 120, thereby allowing rotation of lock member 130 and nut member 140 relative to washer member 120 and bolt member 110.

Figure 9:
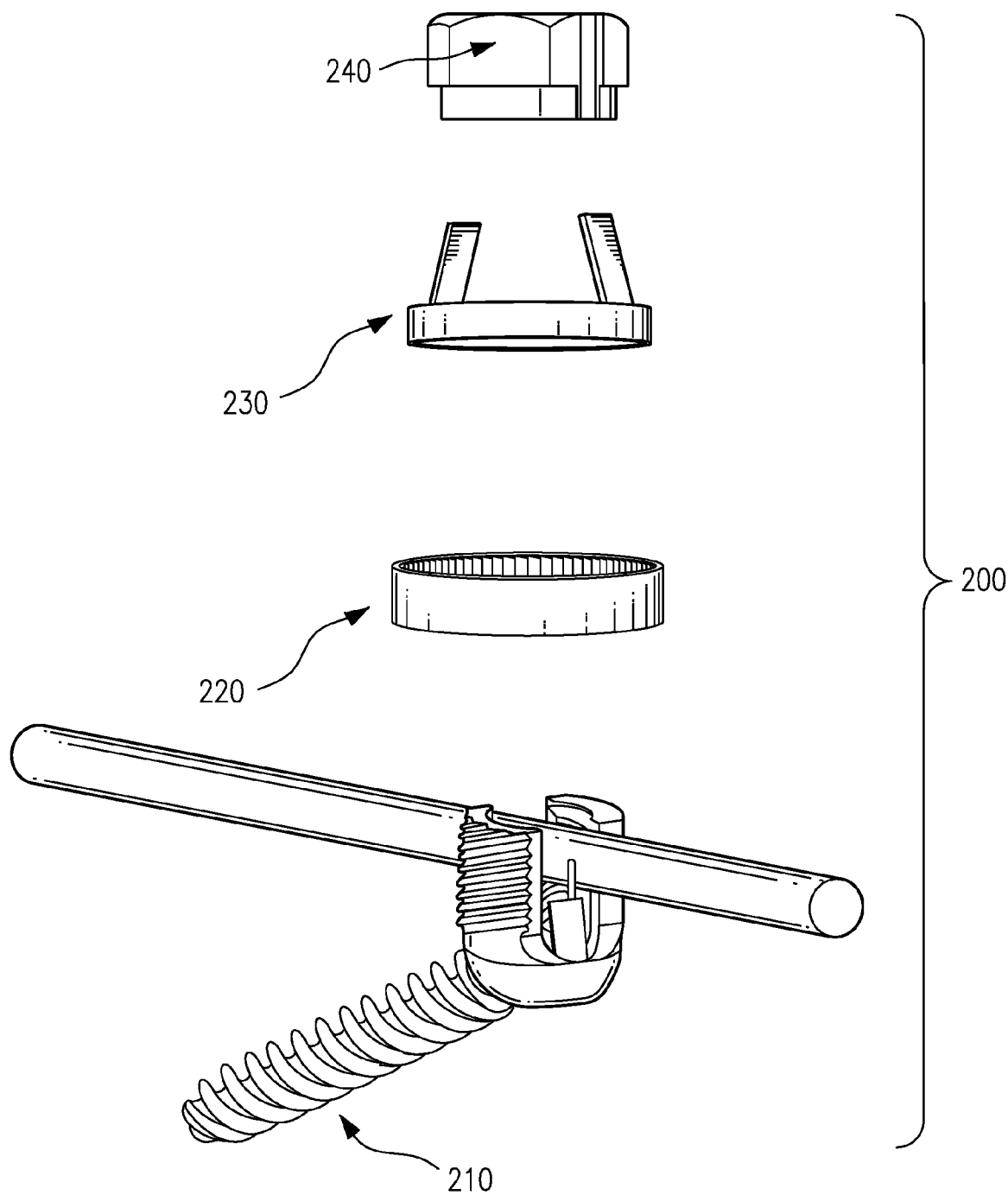
FIG. 9 is an exploded perspective view of another embodiment of fastener device constructed in accordance with the present disclosure, showing a bone fixation system including a locking mechanism in accordance with the present disclosure.

Referring now to FIG. 9, another embodiment of a fastener with a locking mechanism constructed in accordance with the present disclosure designated generally by reference numeral 200. Fastener 200 is similar to fastener 100 and generally includes an elongated bolt member 210, a washer member 220, a lock member 230, and a nut member 240. Nut member 240 is similar to nut member 140 (shown in FIG. 6). Lock member 230 is similar to lock member 130 (shown in FIG. 5).

Figure 10:
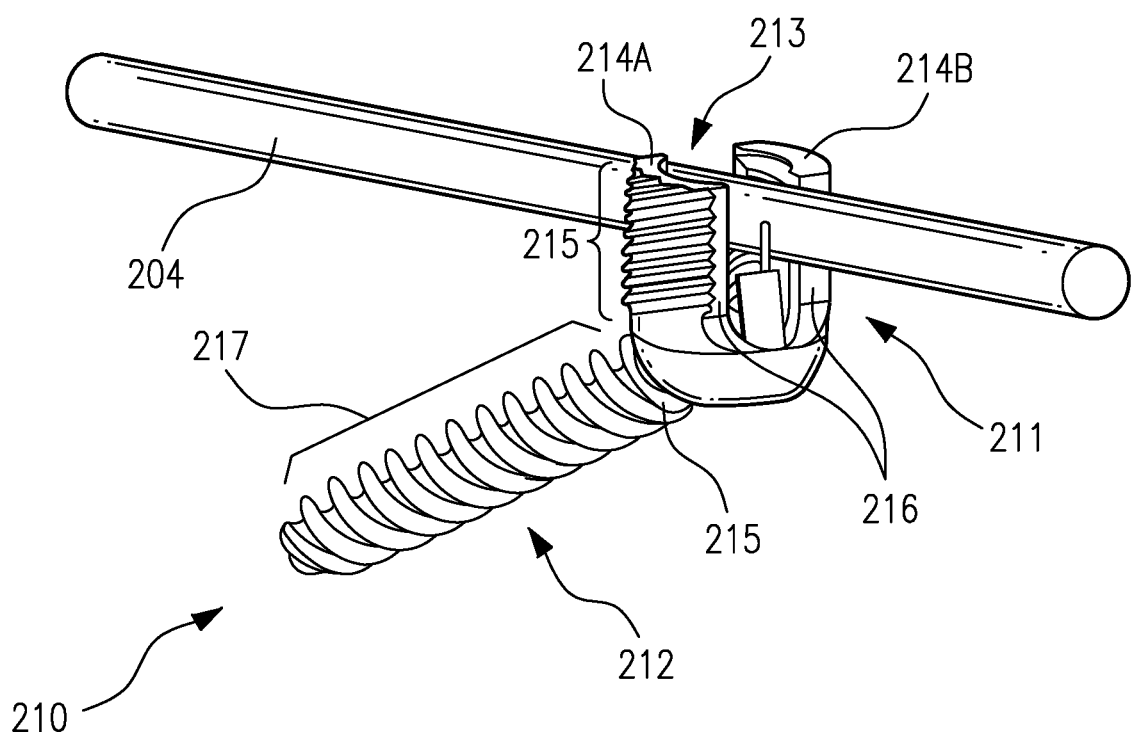
FIG. 10 is a perspective view of the bolt member of FIG. 9, showing the bolt member stem and tulip head.

With reference to FIG. 10, bolt member 210 is similar to bolt member 110, and is additionally configured as fixation system for coupling a rod 204 to bone, for example as a spinal pedicle screw rod system. Bolt member 210 includes a tulip head 211 and an elongated stem 212. Elongated stem 212 includes a second threaded segment 217 that tapers from an end adjacent to tulip head 211 to an end opposite tulip head 211, thereby facilitating insertion of elongated stem 212 into bone structure, such as a pedicle.

Tulip head 211 includes a lateral slot 213 with a first prong 214A and an opposed second prong 214B. Tulip head 211 has a first threaded segment 215 with a banking feature 216. First threaded segment 215 has male threads that correspond to female threads defined within the central bore of nut member 240 (shown in FIG. 9). Banking feature 216 complements the banking feature of washer member 220 (shown in FIG. 11) such that washer member 220 is rotatably fixed and axially displaceable relative to tulip head 211. Banking feature 216 is split by lateral slot 213, thereby allowing for rod 204 to seat therein and to extend therethrough, allowing for rod 204 to be rotationally fixed and axially displaceable relative to tulip head 211.

Figure 11:
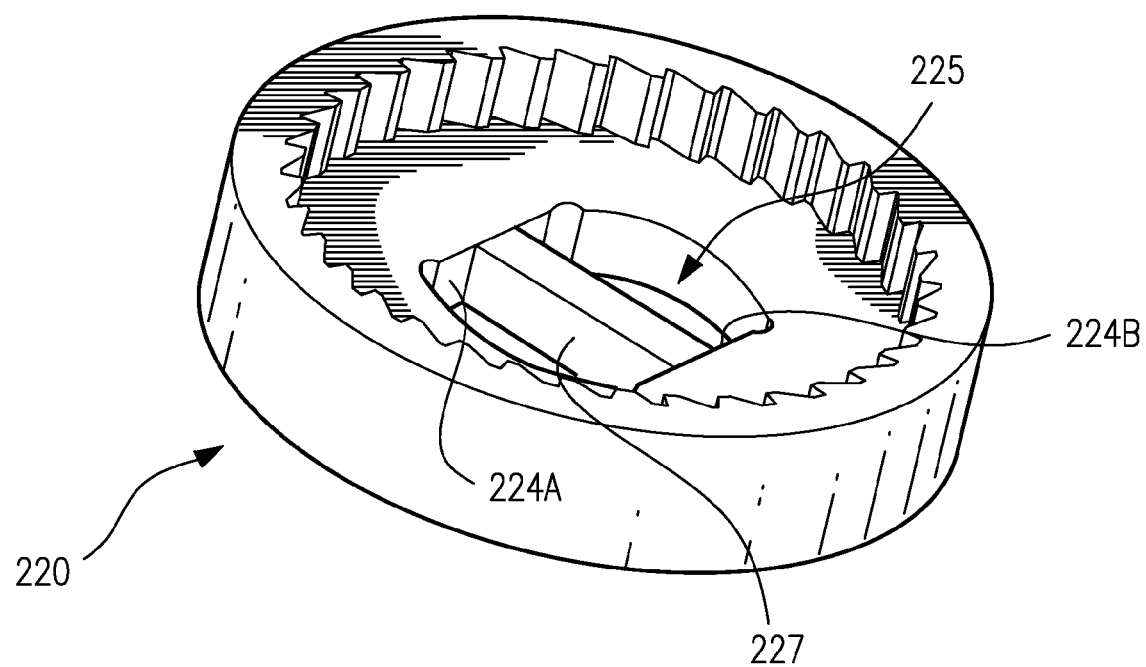
FIG. 11 is a perspective view of the washer member of FIG. 9, showing the washer member central bar portion.

With reference now to FIG. 11, washer member 220 is shown. Washer member 220 is similar to washer member 120 and additionally includes a central bar portion 227. Central bar portion 227 is disposed within washer member central aperture 225 and extends between first flat 224A and second flat 224B of washer member banking portion 224. In this respect central bar portion 227 spans central aperture 225, allowing transfer of force from nut member 240 (shown in FIG. 9) in a force flow path including central bar portion 227 to rod 204 (shown in FIG. 10). As will be appreciated, central bar portion 227 extends between opposing sides of lateral slot 213 to create two discrete axial apertures on diametrically opposed flats of the tulip head banking feature.

Referring to FIGS. 9-11, the flats on first prong 214A (shown in FIG. 10) and second prong 214B are configured to mate with respective first flat inner surface 224A or second inner surface 224B of washer member 220. This rotationally fixes washer member 220 relative to tulip head 211 when first prong 214A and second prong 214B of tulip head 211 are inserted into the discrete axial apertures bounded by central bar portion 227. This allows axial movement of washer member 220 along the prongs of tulip head 211 to secure rod 204 within lateral slot 213 between washer member 220, lock member 230, and tulip head 211. After rod 204 is placed within lateral slot 213, washer member 220 is inserted over prongs of tulip head 211, and central bar portion 227 displaces axially downward within lateral slot 213 response to downward axial displacement of nut member 240 to rest against rod 204.

Those skilled in the art will readily appreciate that because nut member 240 and washer member 220 are substantially similar to nut member 140 and washer member 120, a common tool such as a wrench or socket can be used to tighten rod 204 to the fastener 100 or remove rod 204 from fastener 100 by either rotating nut member 240 clockwise or counterclockwise. Traditional bone fixation systems tend to require a significant amount of torque in order to lock a rod to a fastener or to remove the rod from the fastener. This can be the case, for example, in conventional external bone fixation systems and/or internal bone fixation systems like spinal pedicle screw rod systems. Those skilled in the art will readily appreciate, however, that embodiments of the present invention reduce the amount of torque required as compared with traditional spinal pedicle screw rod systems.

Figure 12:
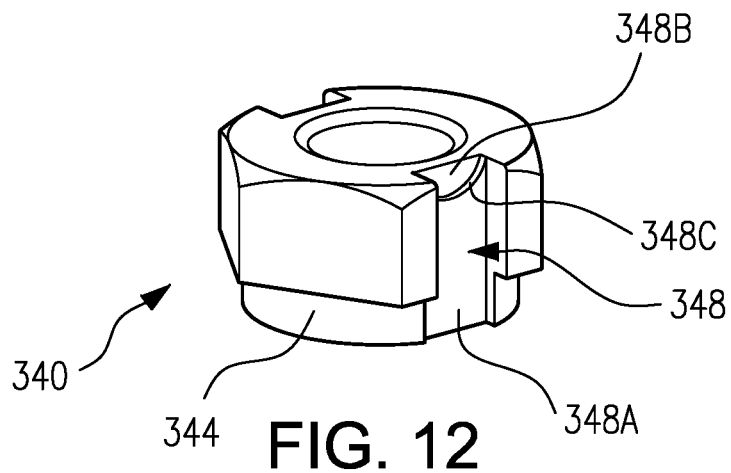
FIGS. 12-14 are perspective views of embodiments of nut member and lock member for the fasteners described herein, showing spring member protrusions and corresponding protrusion sockets define within the nut member axial slots.
Figure 13:
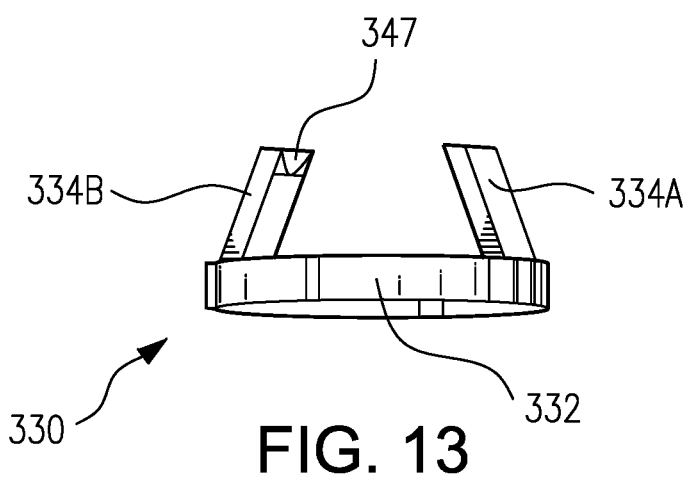
Figure 14:
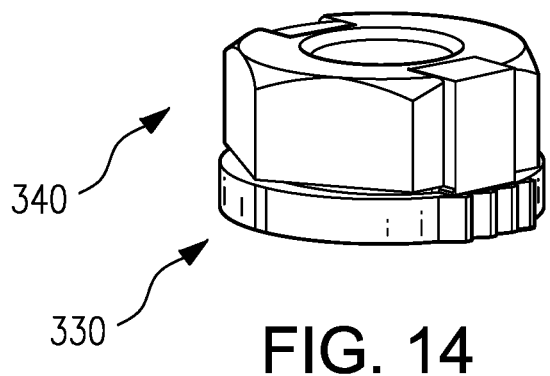

With reference to FIGS. 12-14, a nut member 340 and a lock member 330 are shown according to another embodiment. Referring to FIG. 12, nut member 340 is shown. Nut member 340 is similar to nut member 140 (shown in FIG. 6) and additionally includes a stepped axial slot 348. Stepped axial slot 348 has a first step 348A and a second step 348B. First step 348A traverses annular groove 344 and extends axially to second step 348B. Second step 348B is disposed radially inward of first step 348A. An arcuate riser 348C extends radially outward and faces axially.

Referring to FIG. 13, lock member 330 is shown. Lock member 330 is similar to lock member 130 (shown in FIG. 5) and additionally includes a stiffened deformable annular body 332, a stiffened first spring finger 334A, and a stiffened second spring finger 334B. As used herein, stiffened means that deforming annular body 332, first spring finger 334A, and/or second spring finger 334B requires more force than annular body 132, first spring finger 134, and/or second spring finger 136 (each shown in FIG. 5). This may be accomplished, for example, by thickening the respective elements relative to the counterpart elements shown in the embodiment illustrated in FIG. 5.

First spring finger 334A and second spring finger 334 both include a protrusion 347 (only one indicated in FIG. 13 for clarity reasons). Protrusion 347 corresponds second step 348B of stepped axial slot 348 (shown in FIG. 12), and in illustrated exemplary embodiment has an arcuate lip contoured to complement arcuate riser 348C (shown in FIG. 12) such that arcuate riser 348C seats in second step 348B (shown in FIG. 12). This allows for lock member 330 to seat against 340 and remain in an assembled configuration (shown in FIG. 14) prior to installation on a bolt member, simplifying fastening elements and error proofing the installation process.

Figure 15:
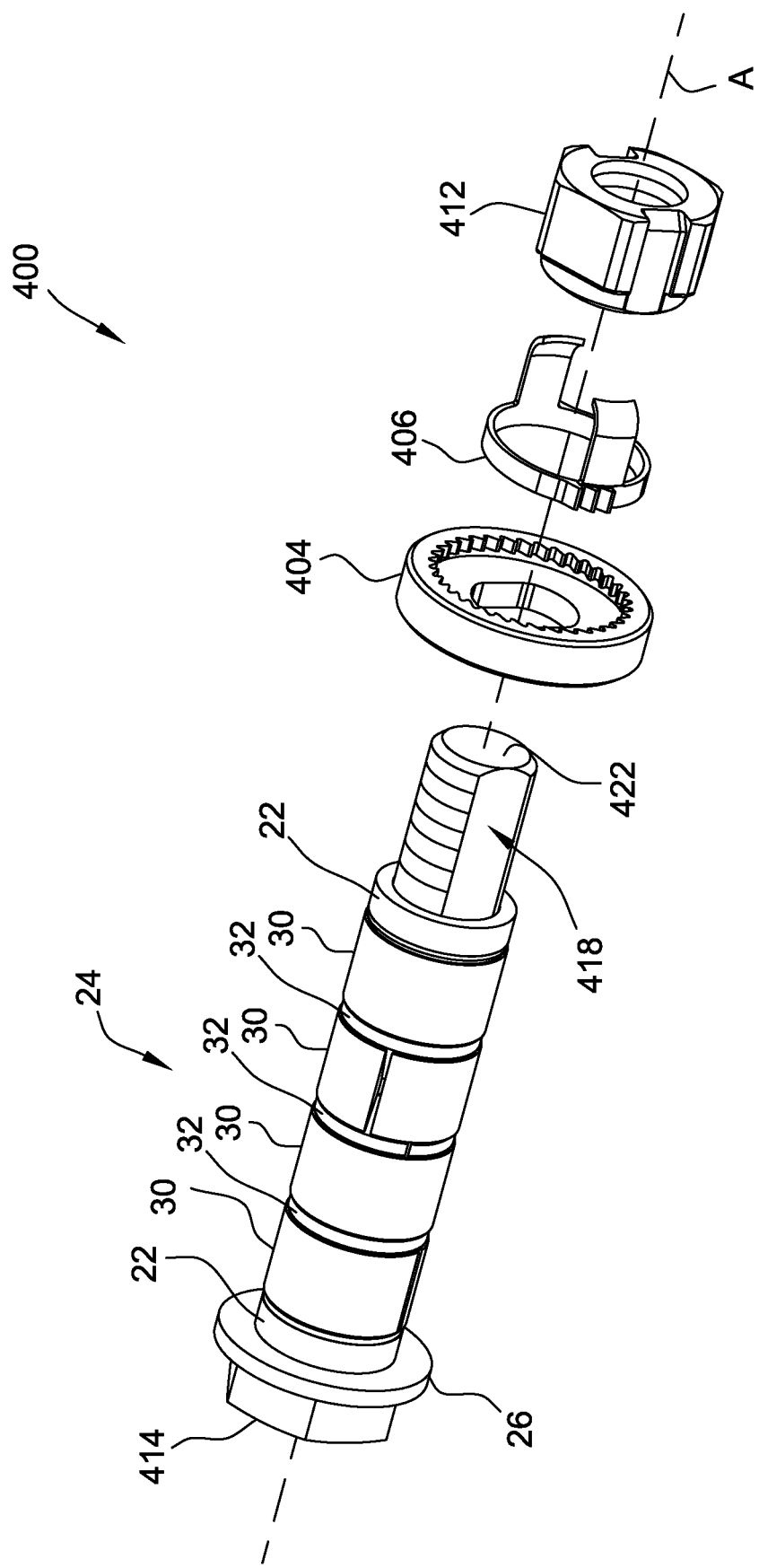
FIG. 15 is an exploded perspective view of an adjustable diameter fastener assembly.
Figure 16:
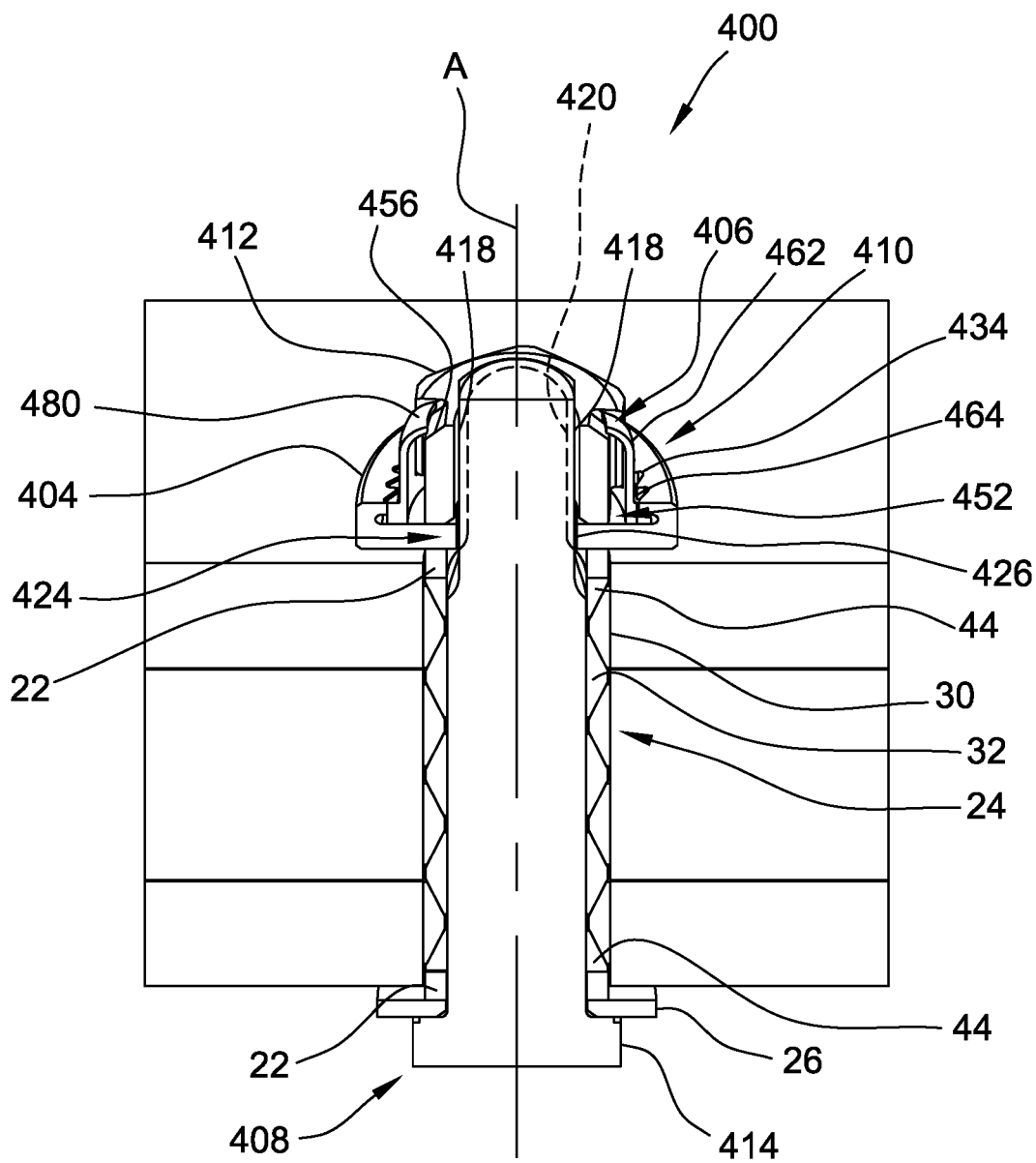
FIG. 16 is a sectional perspective view of the adjustable diameter fastener assembly shown in FIG. 15 in a first orientation, including a lock washer engaged with a lock member and rotationally fixed with respect to a threaded member.
Figure 17:
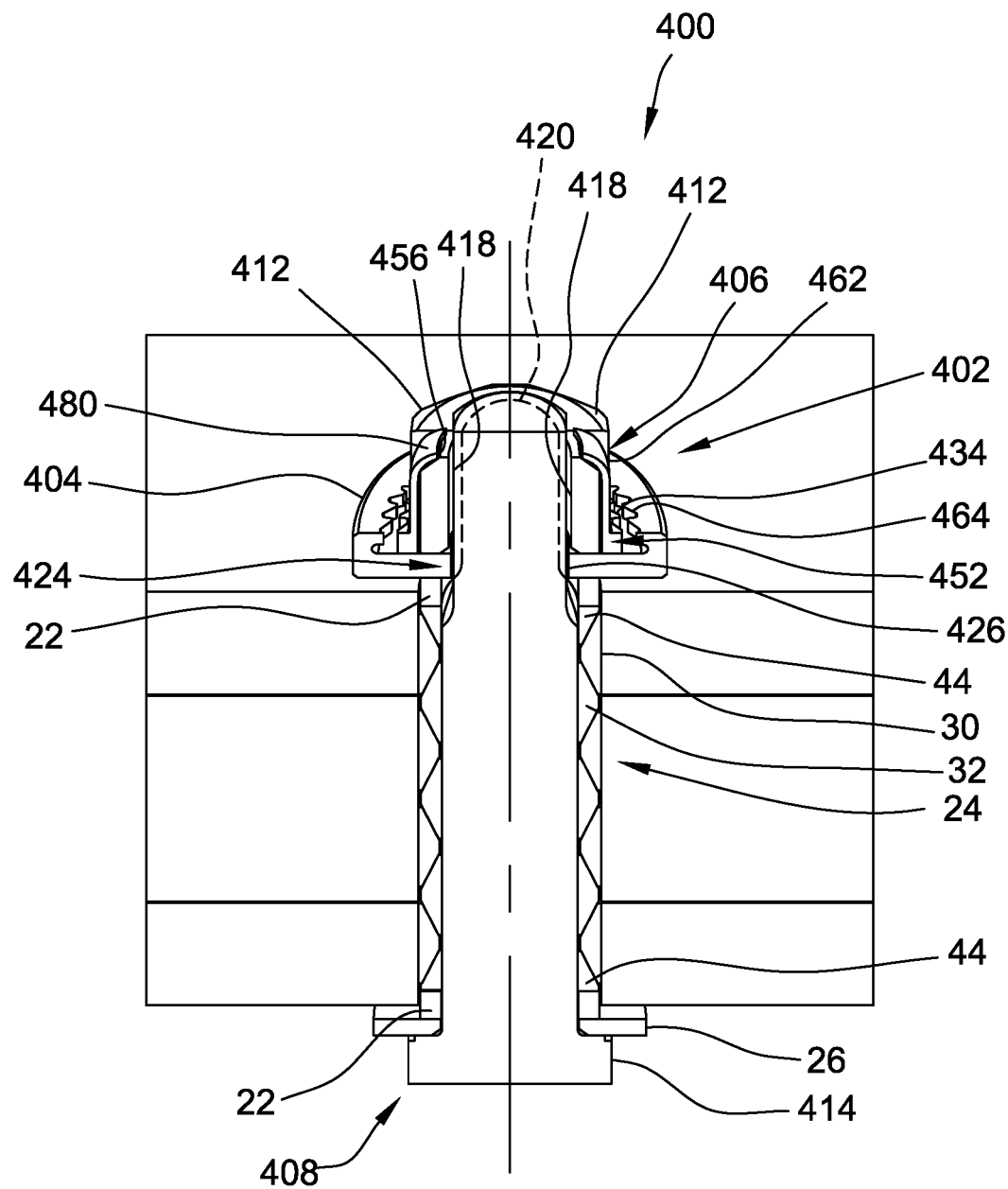
FIG. 17 is a sectional perspective view of the adjustable diameter fastener assembly shown in FIG. 15 in a second orientation, including the lock member disengaged from the lock washer.

FIG. 15 is an exploded perspective view of an adjustable diameter fastener assembly 400. FIG. 16 is a sectional perspective view of adjustable diameter fastener assembly 400 in a first orientation 402, showing a lock washer 404 engaged with a lock member 406 and rotationally fixed with respect to a threaded member 408. FIG. 17 is a sectional perspective view of adjustable diameter fastener assembly 400 in a second orientation 410, showing lock member 406 disengaged from lock washer 404. In the exemplary embodiment, adjustable diameter fastener assembly 400 is an adjustable bushing fastener that operates by radial expansion of a radially expandable bushing 24. Alternatively, adjustable diameter fastener assembly 400 is any type of adjustable diameter fastener assembly, for example, and without limitation, a compression or clamp-up type fastener assembly.

In the exemplary embodiment, radially adjustable bushing 24 is positioned about threaded member 408, between a thrust ring 22 adjacent a head portion 414 and a thrust ring 22 proximate a threaded portion 420 of threaded member 408. A thrust washer 26 is positioned between head portion 414 and thrust ring 22. Bushing 24 includes a plurality of inner rings 32 positioned between outer rings 30. As is known in the art, inner rings 32 have opposed conical wedge surfaces. Outer rings 30 have an exterior cylindrical surface and interior opposed conical wedge surfaces that correspond to the conical wedge surfaces of inner rings 32. Outer rings 30 engage inner rings 32 at opposite ends thereof. Inner rings 32 and outer rings 30 are each split by a slot that extends through a wall of each ring, where the slot extends axially with respect to the rings. The axial ends of bushing 24 are formed by half segments 44 of inner rings 32 to facilitate providing flat end of bushing 24. Alternatively, the ends of bushing 24 can be formed by half segments of outer rings 30, or one end of bushing 24 can be formed by a half segment of inner ring 32 and the other end by a half segment of outer ring 30. It should be appreciated that the geometry of conical wedge surfaces of outer rings 30 and inner rings 32 can be varied, including a cross-sectional shape. Varying the cross-sectional shapes of outer rings 30 and inner rings 32 facilitates configuring outer rings 30 and inner rings 32 to expand in a predetermined manner, for example, and without limitation, having inner rings 32 expand more and/or sooner than outer rings 30.

Figure 18:
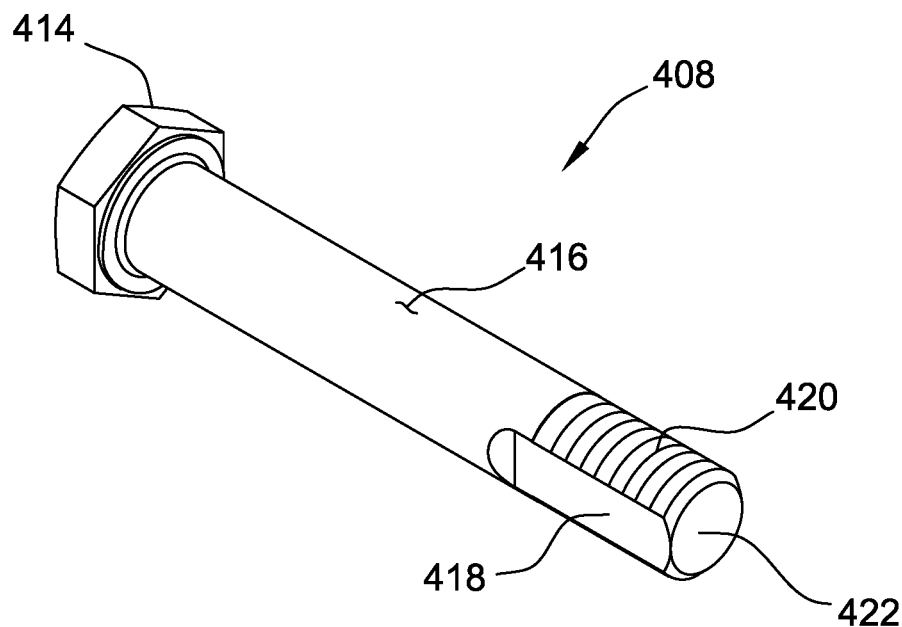
FIG. 18 is a perspective view of a threaded member of the adjustable diameter fastener assembly shown in FIG. 15.
Figure 19:
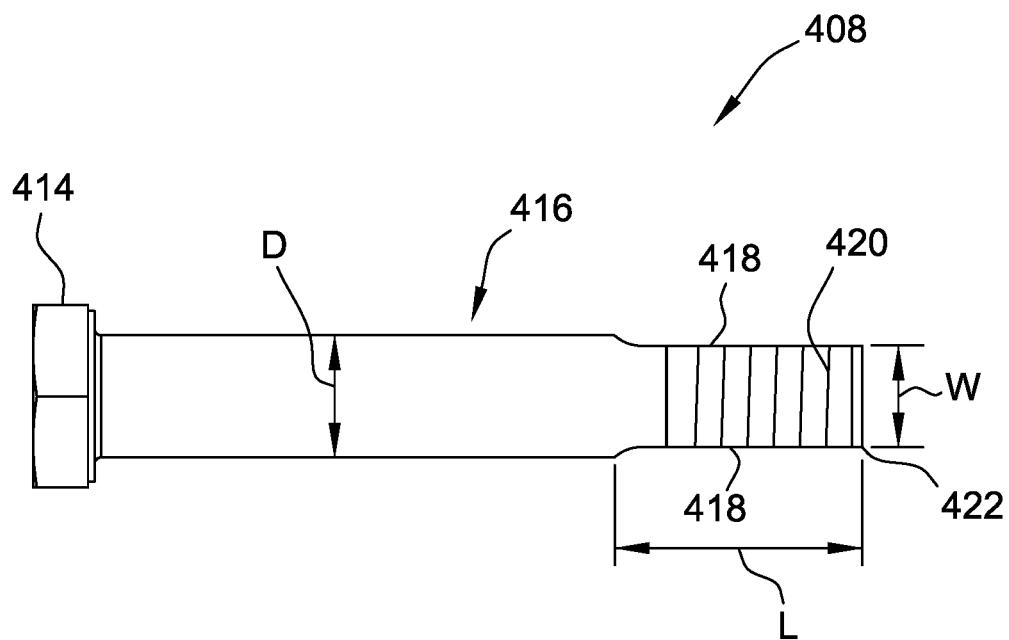
FIG. 19 is a side view of the threaded member shown in FIG. 18.

In the exemplary embodiment, adjustable diameter fastener assembly 400 includes lock washer 404, lock member 406, threaded member 408, and a lock nut 412. FIG. 18 is a perspective view of threaded member 408, and FIG. 19 is a side view of threaded member 408. Threaded member 408 includes head portion 414, an elongated body portion 416 extending axially from head portion 414, and at least one anti-rotation feature 418. Alternatively, threaded member 408 may be free of head portion 414. For example, and without limitation, threaded member 408 may be a rod, a bolt, a screw, or any other threaded component that enables adjustable diameter fastener assembly 400 to function as described herein.

In the exemplary embodiment, anti-rotation feature 418 includes a pair of opposing longitudinally extending sections formed in a threaded portion 420 of body portion 416. It is contemplated that anti-rotation features 418 include, for example, and without limitation, flats, notches, grooves, and/or any other feature that enables threaded member 408 to function as described herein. Body portion 416 has a diameter "D," defining a size of threaded member 408. In the exemplary embodiment, anti-rotation features 418 include a pair of flat portions that are parallel to each other and are spaced apart a width "W," which is smaller than diameter "D." Anti-rotation features 418 are substantially equal in size and shape, and extend along threaded portion 420 of body portion 416 from an end 422 of threaded member 408 a predefined length "L." It is contemplated that anti-rotation features 418 can extend any length "L" along body portion 416, up to and including extend to head portion 414. In the exemplary embodiment, as shown in FIG. 18, head portion 414 is a hexagonal head. Alternatively, head portion 414 is any shape or form, for example, and without limitation, a spline head, a flat head, a socket cap head, a tulip head, and a pan head, that enables adjustable diameter fastener assembly 400 to function as described herein.

Figure 20:
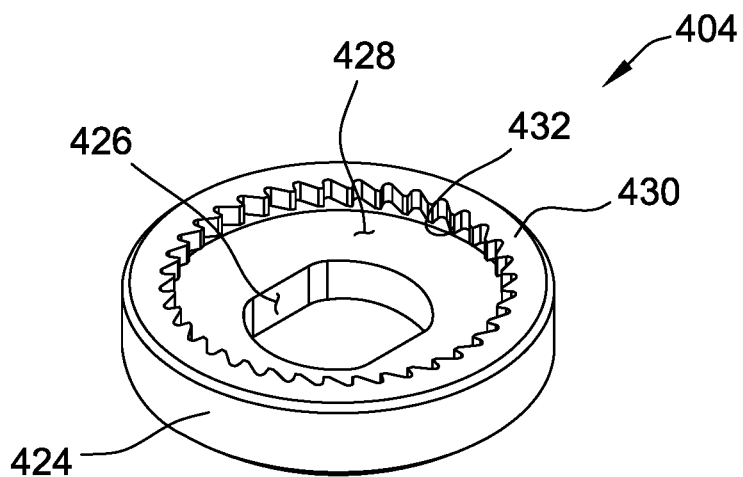
FIG. 20 is a perspective view of a lock washer of the adjustable diameter fastener assembly shown in FIG. 15.
Figure 21:
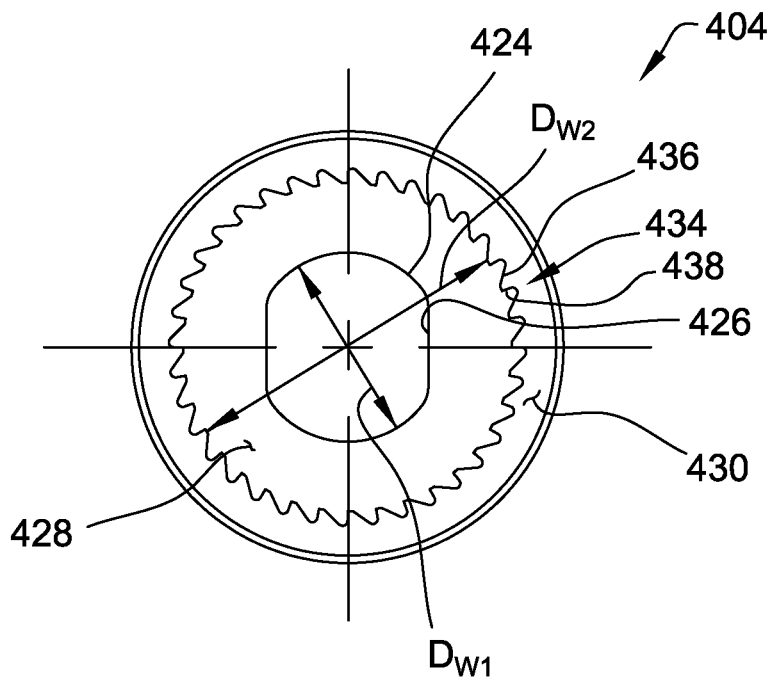
FIG. 21 is a top plan view of the lock washer shown in FIG. 20.

FIG. 20 is a perspective view of lock washer 404, and FIG. 21 is a top plan view of lock washer 404. In the exemplary embodiment, lock washer 404 is configured to slidably couple to anti-rotation features 418 for axial movement along threaded member 408. Anti-rotation features 418 facilitate rotationally fixing lock washer 404 relative to the threaded member 408. Lock washer 404 includes an axial aperture 424 that extends through lock washer 404. Axial aperture 424 is sized to facilitate freely sliding lock washer 404 onto body portion 416 of threaded member 408. As such, axial aperture 424 has a diameter "$D_{w1}$" slightly greater than diameter "D" of body portion 416. Axial aperture 424 also includes an anti-rotation structure 426 configured to engage anti-rotation feature 418 of threaded member 408. It is contemplated that anti-rotation structure 426 includes, for example, and without limitation, a finger, a member, flats, notches, grooves, and/or any other component configured to engage anti-rotation feature 418. In the exemplary embodiment, anti-rotation structure 426 includes a pair of opposing flat inner surfaces sized and shaped to correspond to the pair of opposing longitudinally extending anti-rotation features 418 of body portion 416. Anti-rotation features 418 slidably couple with anti-rotation structures 426 of lock washer 404 to rotationally fix lock washer 404 when body portion 416 is inserted in axial aperture 424. As such, lock washer 404 moves freely along body portion 416 in the axial direction.

Lock washer 404 also includes a central portion 428 surrounding axial aperture 424 and configured to contact a bottom surface 443 (shown in FIG. 23) of lock nut 412 (shown in FIG. 23) in face-to-face contact. A circumferential wall 430 extends axially-upward from central portion 428 about a periphery of lock washer 404. Circumferential wall 430 has a radially-inner surface 432 that defines inner cavity diameter "$D_{w2}$" of lock washer 404. Inner cavity diameter "$D_{w2}$" is sized to receive an annular body 460 (shown in FIG. 24) of lock member 406 (shown in FIG. 24) therein. Circumferential wall 430 has a plurality of notches 434, or locking teeth, defined in radially-inner surface 432 of circumferential wall 430. In the exemplary embodiment, each notch 434 is defined by a sliding surface 436, securing surface 438, and radially-inner surface 432, and is configured to correspond to a sliding surface 484 (shown in FIG. 25) and a securing surface 486 (shown in FIG. 25), respectively, of a respective tooth 464 (shown in FIG. 25) of lock member 406. In particular, securing surface 438 is substantially orthogonal to radially-inner surface 432 and configured to contact securing surface 486 of tooth 464 in face-to-face contact. Sliding surface 436 is formed oblique to radially-inner surface 432 configured to contact sliding surface 484 of tooth 464 in face-to-face contact.

In the exemplary embodiment, lock washer 404 is fabricated from a metal, for example, and without limitation, steel, aluminum, titanium, or a superalloy. Alternatively, lock washer 404 is fabricated from any material that enables adjustable diameter fastener assembly 400 to function as described herein, such as, for example, and without limitation, composite materials, resins, fiber reinforced resins, plastics, and fiber reinforced plastics.

Figure 22:
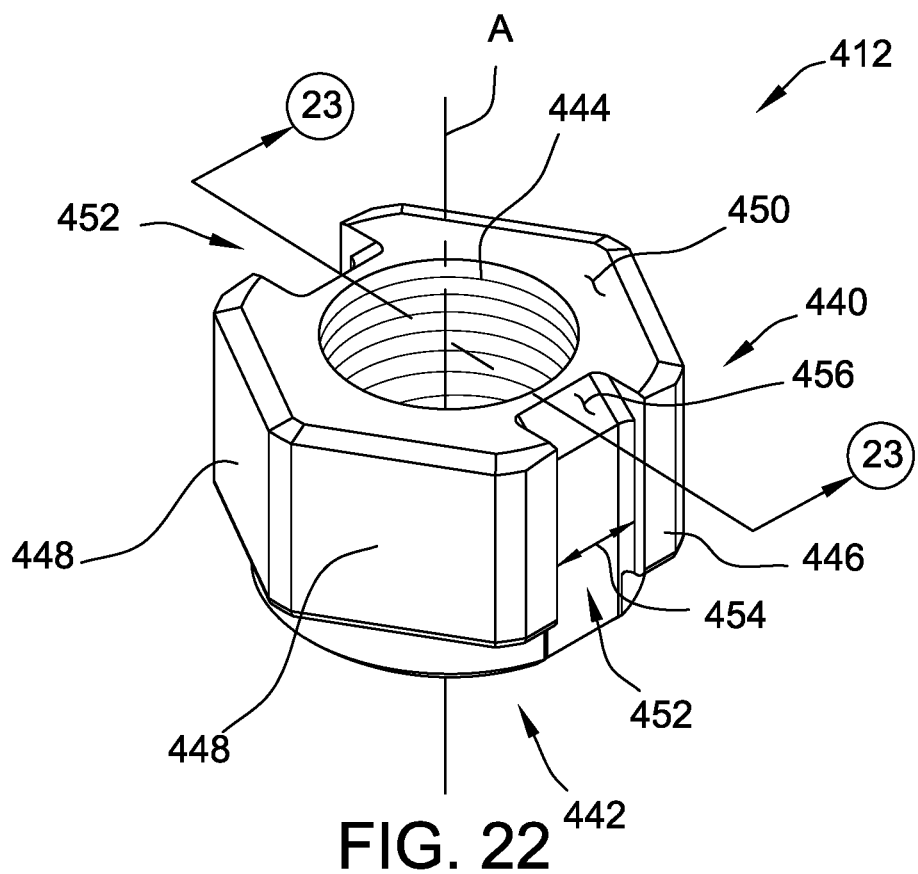
FIG. 22 is a perspective view of a lock nut of the adjustable diameter fastener assembly shown in FIG. 15.
Figure 23:
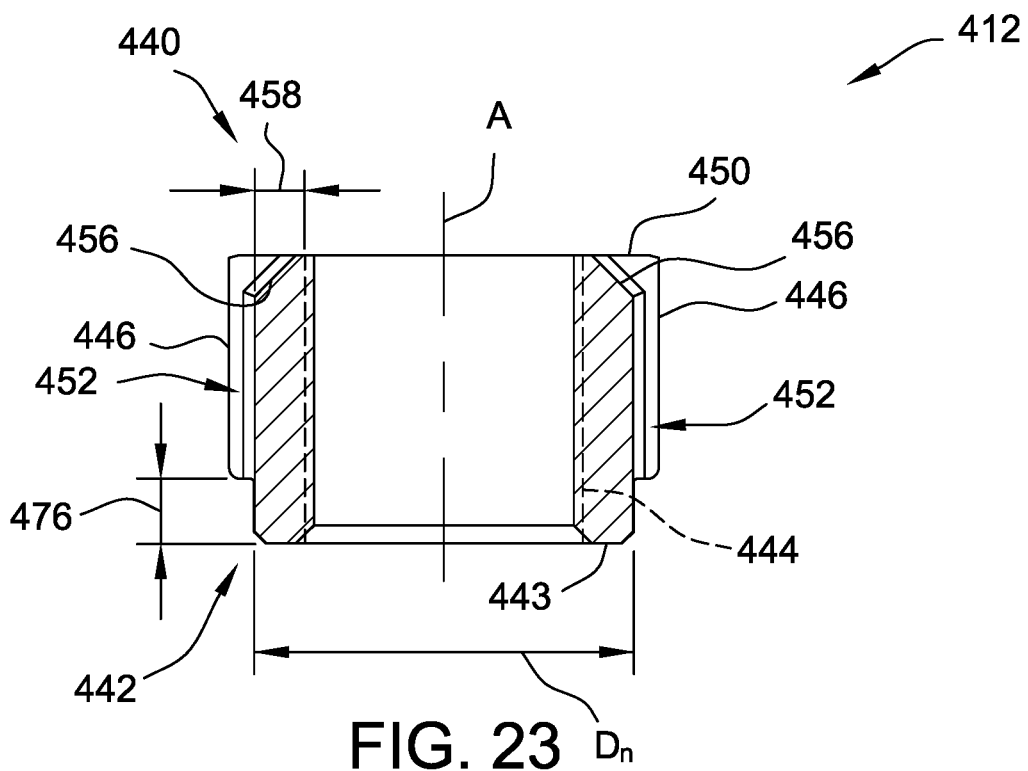
FIG. 23 is a sectional view of the lock nut shown in FIG. 22 taken through line 23-23.

FIG. 22 is a perspective view of lock nut 412, and FIG. 23 is a sectional view of lock nut 412 taken through line 23-23 (shown in FIG. 22). In the exemplary embodiment, lock nut 412 includes a head portion 440 and a shoulder portion 442 extending axially from head portion 440 along longitudinal axis "A." A female threaded portion 444 extends through lock nut 412 and is formed about longitudinal axis "A." Head portion 440 includes one or more slotted circumferential faces 446 and one or more continuous faces 448. Slotted circumferential faces 446 and continuous faces 448, combined, define tool engagement surfaces that extend substantially axially between shoulder portion 442 and a top surface 450 of lock nut 412, opposite shoulder portion 442. The tool engagement surfaces are configured in a hexagonal-shaped arrangement, although other configurations are contemplated. The tool engagement surfaces correspond to one or more tools, for example, and without limitation, a wrench and/or a socket. As such, the tool engagement surfaces facilitate tightening and/or loosening lock nut 412 using common hand tools, and without requiring use of a specialized tool.

In the exemplary embodiment, each slotted circumferential face 446 defines an axial slot 452. Each axial slot 452 extends generally axially along slotted circumferential face 446 from top surface 450 of lock nut 412, and has a circumferential width 454 sized to receive a spring finger 462 (shown in FIG. 24) of lock member 406 (shown in FIG. 24). This facilitates fixing lock member 406 rotationally with respect to lock nut 412 when axial slot 452 is aligned with spring finger 462. In particular, spring finger 462 snaps into axial slot 452 to facilitate coupling lock member 406 to lock nut 412. A top portion 456 of axial slot 452 tapers inward toward longitudinal axis "A" a predetermined distance 458 to define a ledge that receives an ear portion 482 of spring finger 462. This facilitates retaining lock member 406 on lock nut 412 about longitudinal axis "A."

In the exemplary embodiment, lock nut 412 includes two axial slots 452 disposed on diametrically-opposed slotted circumferential faces 446, i.e. on slotted circumferential faces 446 that are substantially parallel to each other and generally positioned symmetrical to each other with respect to longitudinal axis "A." In alternative embodiments, lock nut 412 includes fewer or greater than two axial slots 452, such that, for example, a respective axial slot 452 is circumferentially-positioned relative to a respective spring finger 462 of lock member 406.

In the exemplary embodiment, lock nut 412 is fabricated from a metal, for example, and without limitation, steel, aluminum, titanium, or a superalloy. Alternatively, lock nut 412 is fabricated from any material that enables adjustable diameter fastener assembly 400 to function as described herein, such as, for example, and without limitation, composite materials, resins, fiber reinforced resins, plastics, and fiber reinforced plastics.

Figure 24:
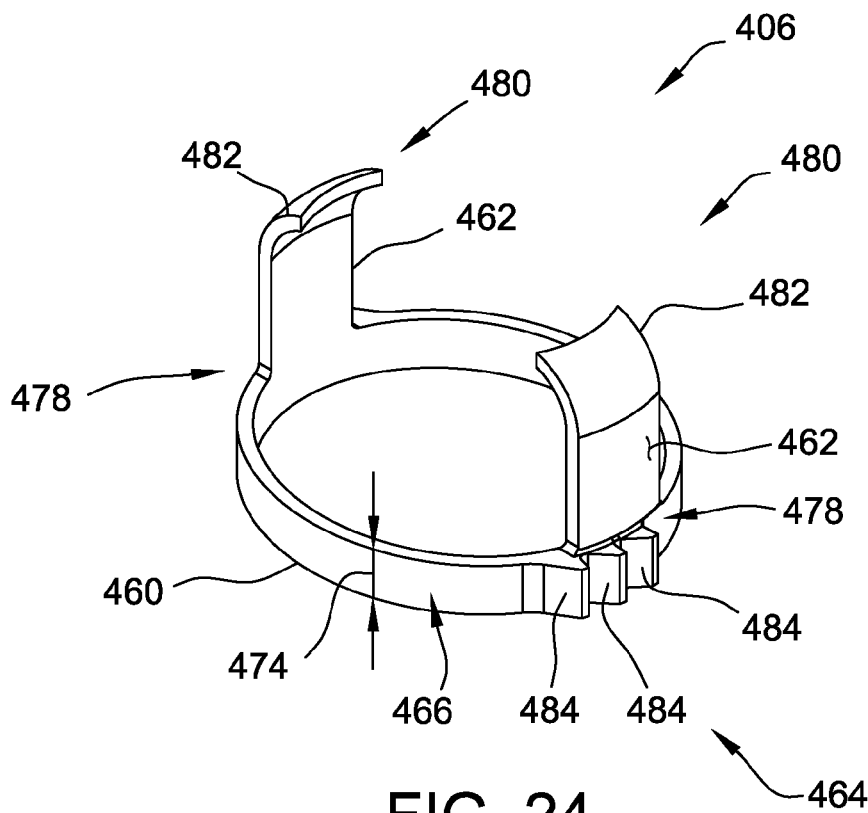
FIG. 24 is a perspective view of a lock member of the adjustable diameter fastener assembly shown in FIG. 15.
Figure 25:
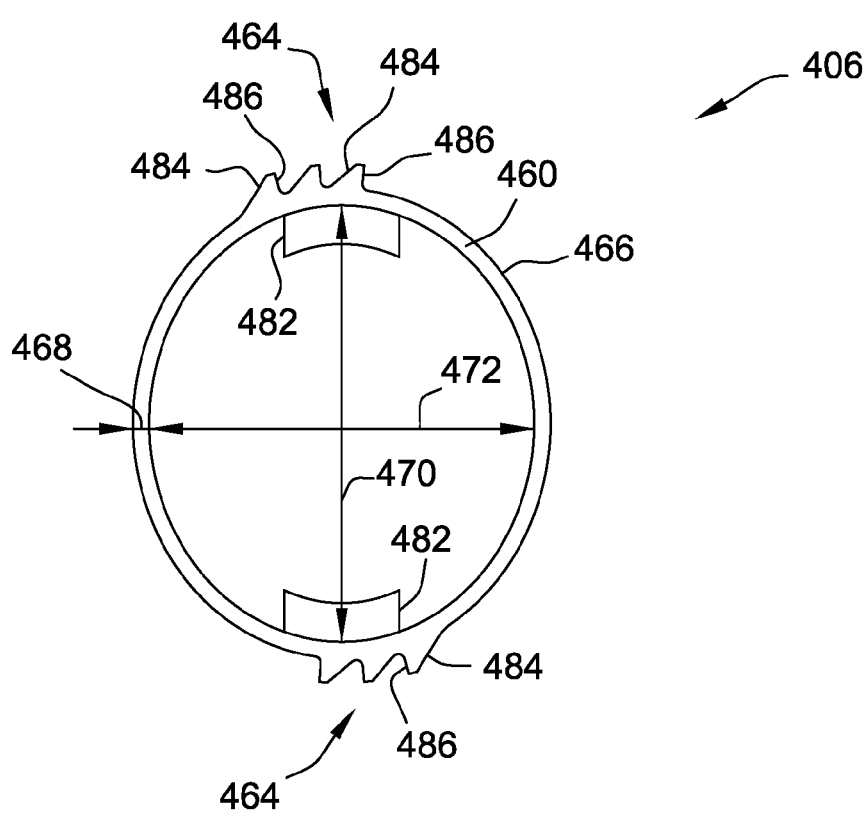
FIG. 25 is a bottom view of the lock member shown in FIG. 24.

FIG. 24 is a perspective view of lock member 406, and FIG. 25 is a bottom view of lock member 406. In the exemplary embodiment, lock member 406 includes a ring-shaped annular body 460 having one or more spring fingers 462 extending generally axially upward from annular body 460. Annular body 460 includes one or more radially-extending teeth 464 (broadly detent members) disposed on an outer surface 466 of annular body 460. In the exemplary embodiment, annular body 460 is a generally oval-shaped ring having a predetermined wall thickness 468, that when combined with an internal major axis length 470, facilitates fitting within inner cavity diameter "$D_{w2}$" (shown in FIG. 21) of lock washer 404 (shown in FIG. 21). Annular body 460 also has a predetermined inner minor axis length 472 that corresponds to a diameter "$D_n$" (shown in FIG. 23) shoulder portion 442 (shown in FIG. 23) of lock nut 412 (shown in FIG. 23) to facilitate coupling lock member 406 to lock nut 412. In the exemplary embodiment, internal major axis length 470 is greater than internal minor axis length 472. Annular body 460 also has a height 474 that is slightly shorter than a height 476 (shown in FIG. 23) of shoulder portion 442 of lock nut 412, such that lock member 406 remains able to be deflected or flexed, as described further herein, when shoulder portion 442 applies an axial force against lock washer 404. In the exemplary embodiment, annular body 460 is deflectable, such that, in response to a radial force exerted thereon by one or more of spring fingers 462, annular body 460 is radially-deflected, becoming more or less circular based upon an amount of the radial force exerted on annular body 460.

It is contemplated that annular body 460 may have shapes other than oval, for example, and without limitation, annular body 460 may be round, ellipsoid, or any other suitable shape. In the exemplary embodiment, annular body 460 is fabricated from a resilient metallic material, such as a spring steel. Alternatively, annular body 460 is fabricated from any resilient material that enables lock member 406 to function as described herein, for example, and without limitation, resilient composite materials, resins, fiber reinforced resins, plastics, and fiber reinforced plastics.

In the exemplary embodiment, each spring finger 462 extends axially upward from annular body 460 from a fixed end 478 to a free end 480. Fixed end 478 is coupled to annular body 460. Free end 480 extends radially inward and defines an ear portion 482. Ear portion 482 extends radially inward such that when coupled to lock nut 412, ear portion 482 extends over top portion 456 (shown in FIG. 23) of axial slot 452 (shown in FIG. 23) to facilitate retaining lock member 406 on lock nut 412. In one embodiment, free end 480 curves inward to form ear portion 482. Alternatively, free end 480 is bent and/or slanted radially inward to define ear portion 482, or otherwise extends radially-inward in any manner that enables lock member 406 to function described herein. In the exemplary embodiment, each spring finger 462 is formed substantially the same. While lock member 406 is described with two spring fingers 462, in alternative embodiments, lock member 406 includes fewer or greater than two spring fingers 462, such that, for example, a respective spring finger 462 is circumferentially-positioned relative to a respective axial slot 452 of lock nut 412.

As described above, one or more radially-extending teeth 464 (or detent members) are disposed on outer surface 466 of annular body 460. In particular, in the exemplary embodiment, sets of three adjacent radially-extending teeth 464 are disposed on annular body 460 with each set generally circumferentially aligned relative to a respective spring finger 462. Each tooth 464 includes a sliding surface 484 and a securing surface 486. Sliding surface 484 and securing surface 486 are sized and shaped to correspond to sliding surface 436 (shown in FIG. 21) and securing surface 438 (shown in FIG. 21), respectively, of notches 434 (shown in FIG. 21) of lock washer 404. In the exemplary embodiment, radially-extending teeth 464 are configured to facilitate preventing rotation that affects loosening of lock nut 412 with respect to lock washer 404, for example, rotation in a counter-clockwise direction. Alternatively, radially-extending teeth 464 are configured to facilitate preventing rotation of lock nut 412 in the clockwise direction, or both the counter-clockwise and the clockwise directions. While lock member 406 is described with three radially-extending teeth 464 formed proximate each spring finger 462, in alternative embodiments, lock member 406 includes fewer or greater than three teeth 464.

In operation, with reference to FIG. 16, in first orientation 402, lock washer 404, lock member 406, and lock nut 412 are fixed axially and rotationally relative to threaded member 408. In second orientation 410 shown in FIG. 17, lock member 406 and lock nut 412 are rotationally free relative to threaded member 408. Rotation of lock nut 412 relative to threaded member 408 displaces lock nut 412 and lock member 406 axially relative to threaded member 408, facilitating adjusting the diameter of adjustable diameter fastener assembly 400. In particular, lock nut 412 displaces lock washer 404 axially relative to threaded member 408 such that lock washer 404 applies an axial (or compression) force against thrust ring 22 proximate a threaded portion 420 of threaded member 408. At the opposite end of threaded member 408, thrust washer 26 is seated against a second thrust ring 22. Continued rotation of lock nut 412 facilitates compressing bushing 24 to thus shorten the overall length of bushing 24. As such, inner rings 32 contract and outer rings 30 are forced to expand and assume an increased diameter, thereby facilitating adjusting the outside diameter of bushing 24.

In first orientation 402, threaded portion 420 of threaded member 408 is inserted through axial aperture 424 of lock washer 404 such that anti-rotation structures 426 engage anti-rotation features 418 of threaded member 408, thereby rotationally fixing lock washer 404 relative to threaded member 408. The oval shape of annular body 460 (shown in FIG. 24) facilitates urging radially-extending teeth 464, positioned generally circumferentially aligned relative to a respective spring finger 462, radially-outward and into contact with notches 434 of lock washer 404. In particular, one or more of sliding surfaces 484 and securing surfaces 486 (shown in FIG. 25) of radially-extending teeth 464 are urged into face-to-face contact with sliding surfaces 436 and securing surfaces 438 (shown in FIG. 23), respectively, of notches 434, rotationally fixing lock member 406 relative to lock washer 404.

As shown in FIG. 16, in first orientation 402, free end 480 of spring finger 462 seats within top portion 456 of axial slot 452 of lock nut 412. Seating free end 480 of spring finger 462 in top portion 456 of axial slot 452 facilitates rotationally-fixing lock member 406 with lock nut 412. As such, lock member 406 and lock nut 412 are caused to rotate together. Consequently, when one or more radially-extending teeth 464 of lock member 406 seats against one or more notches 434 of lock washer 404, lock member 406 becomes rotationally-fixed relative to lock washer 404, causing lock nut 412 to become rotationally-fixed relative to lock washer 404 and threaded member 408.

As described above, lock member 406 is captured between lock nut 412 and lock washer 404, and in particular, about shoulder portion 442 (shown in FIG. 22) of lock nut 412. Because height 474 (shown in FIG. 24) of annular body 460 is shorter than height 476 (shown in FIG. 23) of shoulder portion 442 of lock nut 412, lock member 406 can be deflected or flexed as described herein.

In second orientation 410, each spring finger 462 is displaced radially inward to facilitate deflecting annular body 460 (shown in FIG. 24) to disengage radially-extending teeth 464 from notch 434 of lock washer 404. In particular, displacing fixed end 478 (shown in FIG. 24) of spring finger 462 radially inward facilitates disengaging one or more of sliding surfaces 484 and securing surfaces 486 (shown in FIG. 25) of radially-extending teeth 464 from face-to-face contact with sliding surfaces 436 and securing surfaces 438 (shown in FIG. 21), respectively, of notches 434 to facilitate rotation of lock nut 412 and lock member 406 relative to lock washer 404.

To facilitate displacing spring fingers 462 radially inward, as described herein, a tool (not shown), such as a conventional socket or wrench, is coupled to lock nut 412. The tool is axially displaced relative to lock nut 412 where it contacts free end 480 of spring fingers 462. As described above, free end 480 curves inward to form ear portion 482 (shown in FIG. 24). As the tool contacts ear portion 482, spring fingers 462 are radially displaced, facilitating deflecting annular body 460 such that radially-extending teeth 464 are disengaged from notches 434. The tool may be rotated either clockwise or counterclockwise about longitudinal axis "A" to displace lock nut 412 axially in either direction along longitudinal axis "A," tightening lock nut 412 or loosening lock nut 412 as appropriate. Thus, when a tool such as a conventional socket or wrench is applied to lock nut 412, lock member 406 is deflected radially inward such that teeth 464 of lock member 406 disengage notches 434 of lock washer 404, thereby allowing rotation of lock member 406 and lock nut 412 relative to lock washer 404 and threaded member 408.

Figure 26:
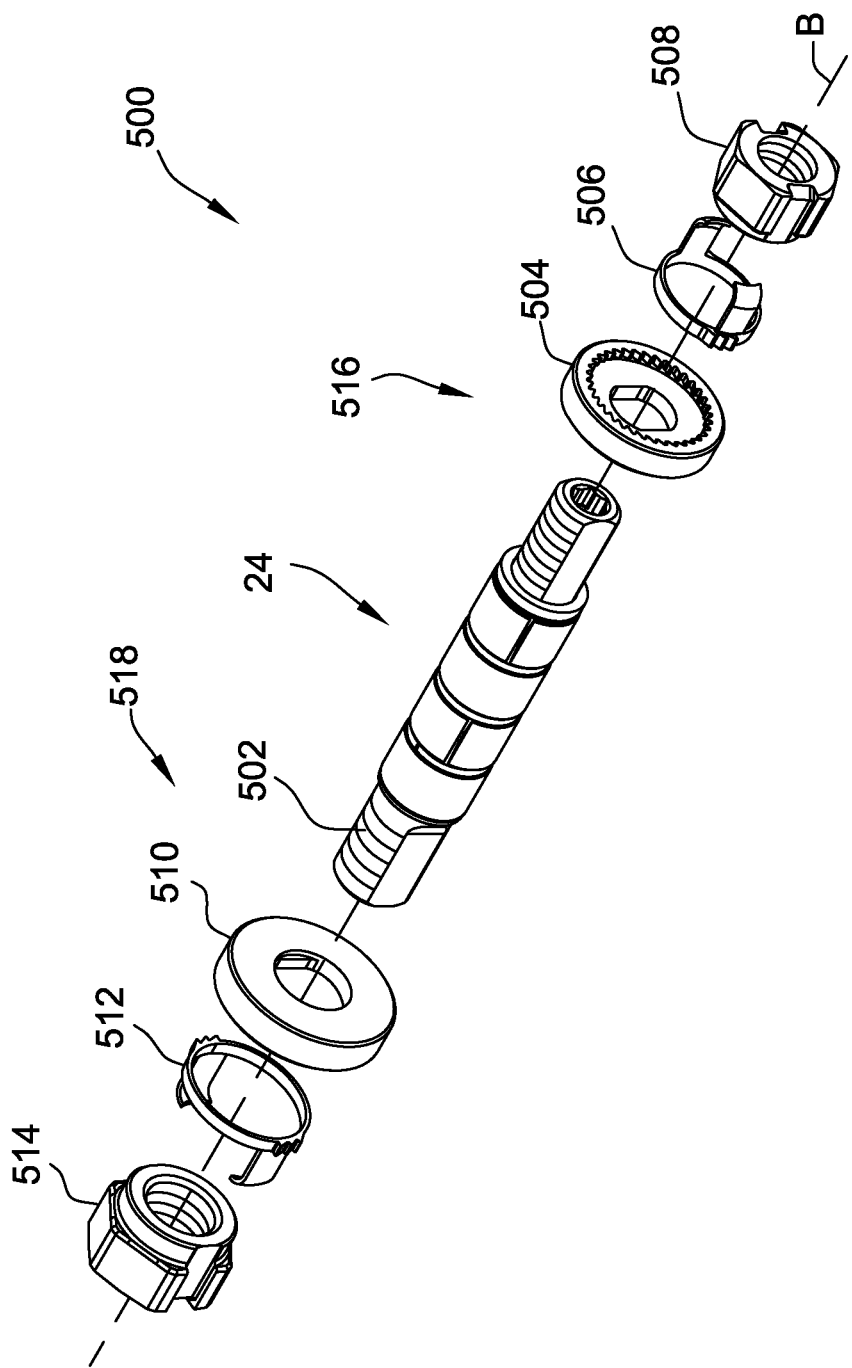
FIG. 26 is an exploded perspective view of an alternative adjustable diameter fastener assembly.

FIG. 26 is an exploded perspective view of an alternative adjustable diameter fastener assembly 500. In the exemplary embodiment, adjustable diameter fastener assembly 500 is similar to adjustable diameter fastener assembly 400 (shown in FIG. 15) and includes a first lock washer 504, a first lock member 506, and a first lock nut 508 proximate a first end 516 of a threaded member 502. In addition, adjustable diameter fastener assembly 500 includes a second lock washer 510, a second lock member 512, and a second lock nut 514 proximate a second end 518 of threaded member 502. In the exemplary embodiment, adjustable diameter fastener assembly 500 is an adjustable diameter clamping bolt of the adjustable bushing fastener type that operates by radial expansion of radially expandable bushing 24. Alternatively, adjustable diameter fastener assembly 500 is any type of adjustable diameter fastener assembly, for example, and without limitation, a compression or clamp-up type fastener assembly.

In the exemplary embodiment, adjustable diameter fastener assembly 500 functions substantially similar to adjustable diameter fastener assembly 400, but includes a second set of locking components in place of head portion 414 (shown in FIG. 15) of threaded member 408 (shown in FIG. 15). In particular, first lock washer 504 and second lock washer 510 are fabricated substantially similar to lock washer 404 (shown in FIG. 15); first lock member 506 and second lock member 512 are fabricated substantially similar to lock member 406 (shown in FIG. 15); and first lock nut 508 and second lock nut 514 are fabricated substantially similar to lock nut 412 (shown in FIG. 15). It is noted that the relative size of the components may differ; however, the general function is substantially the same as adjustable diameter fastener assembly 400. In particular, the rotational fixing of first lock nut 508 and second lock nut 514 is substantially the same as described above for adjustable diameter fastener assembly 400, with respect to FIGS. 16 and 17.

Figure 27:
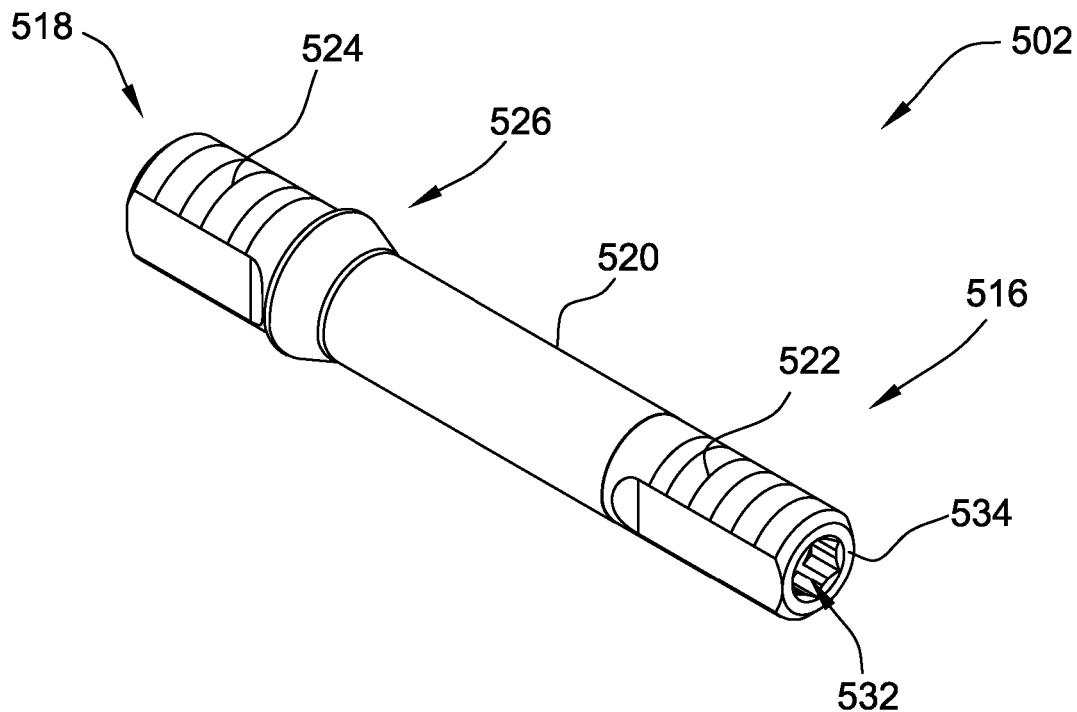
FIG. 27 is a perspective view of a threaded member of the adjustable diameter fastener assembly shown in FIG. 26.
Figure 28:
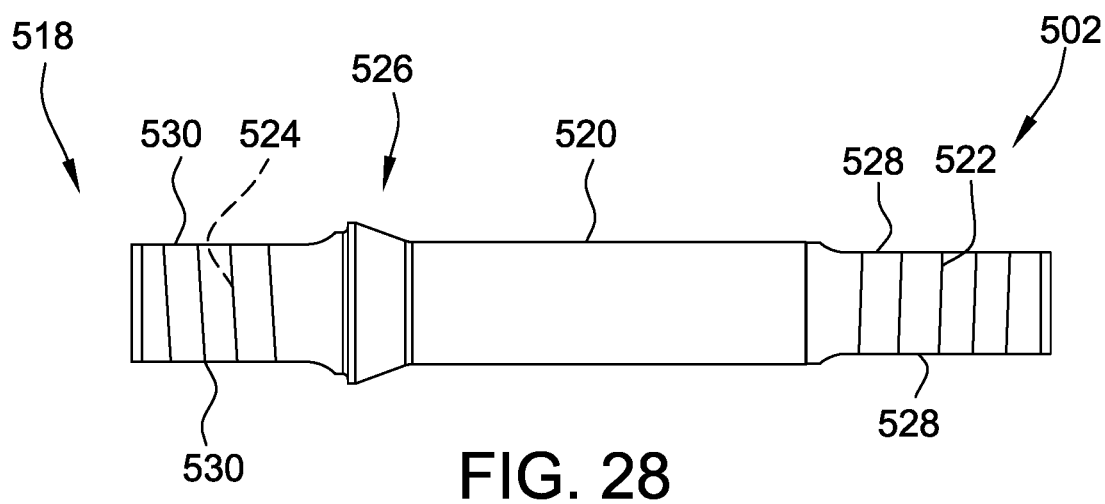
FIG. 28 is a side view of the threaded member shown in FIG. 27.

FIG. 27 is a perspective view of threaded member 502, and FIG. 28 is a side view of threaded member 502. Threaded member 502 includes an elongated body portion 520 extending axially from first end 516 to second end 518. Threaded member 502 also includes a first threaded portion 522 at first end 516, and a second threaded portion 524 at second end 518. A wedge portion 526 is formed proximate second end 518 and is configured to receive a portion of bushing 24 (shown in FIG. 26) to facilitate compression of bushing 24 during use of adjustable diameter fastener assembly 500. At least one first anti-rotation feature 528 is formed at first end 516, and at least one second anti-rotation feature 530 is formed at second end 518.

In the exemplary embodiment, first anti-rotation feature 528 and second anti-rotation feature 530 are formed substantially similar to anti-rotation feature 418 (shown in FIG. 18) and includes a pair of opposing, longitudinally extending sections formed in first threaded portion 522 and second threaded portion 524, respectively. It is contemplated that anti-rotation features 528 and 530 include, for example, and without limitation, flats, notches, grooves, and/or any other feature that enables threaded member 502 to function as described herein. In the exemplary embodiment, first anti-rotation feature 528 includes a pair of flat portions that are parallel to each other, are substantially equal in size and shape, and extend along at least a portion of threaded portion 522. It is contemplated that anti-rotation features 528 can extend any length along body portion 520, up to and including extending to wedge portion 526. In addition, second anti-rotation feature 530 also includes a pair of flat portions that are parallel to each other, are substantially equal in size and shape, and extend along at least a portion of threaded portion 524. It is contemplated that anti-rotation features 530 can extend any length along body portion 520, up to and including extending to wedge portion 526.

In the exemplary embodiment, as shown in FIG. 27, first end 516 of threaded member 502 includes a socket 532 formed in an end face 534 of body portion 520. Socket 532 is formed as a hexagonal socket to facilitate receiving a tool used to secure threaded member 502 against rotation while one or more of lock nuts 508 and 514 are tightened and/or loosened. Alternatively, socket 532 is any shape or form, for example, and without limitation, a spline head and/or a slot, that enables adjustable diameter fastener assembly 500 to function as described herein.

Figure 29:
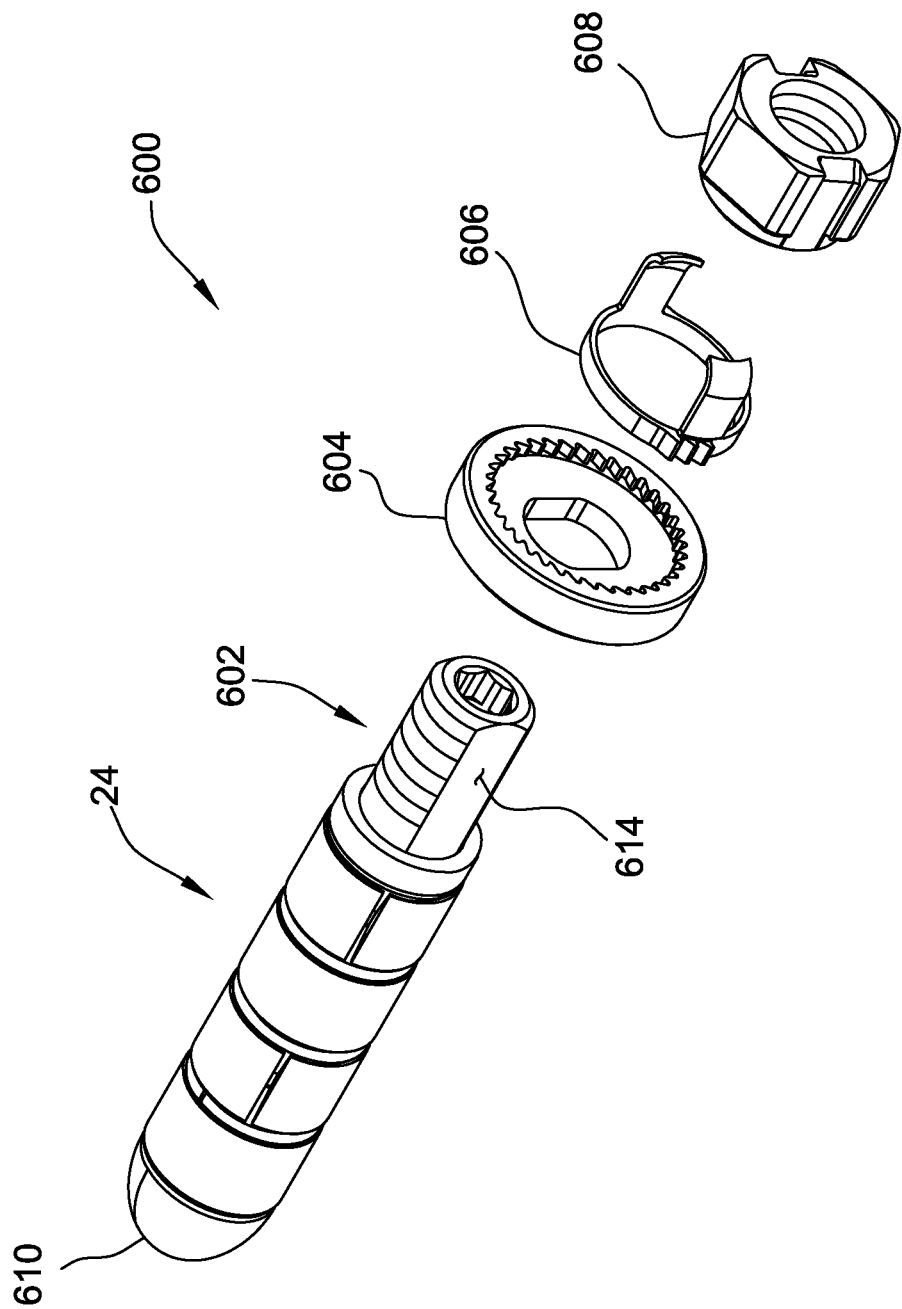
FIG. 29 is an exploded perspective view of another alternative adjustable diameter fastener assembly.

FIG. 29 is an exploded perspective view of an alternative adjustable diameter fastener assembly 600. In the exemplary embodiment, adjustable diameter fastener assembly 600 is similar to adjustable diameter fastener assembly 400 (shown in FIG. 15) and includes a threaded member 602, bushing 24, a lock washer 604, a lock member 606, and a lock nut 608. In the exemplary embodiment, adjustable diameter fastener assembly 600 is an adjustable diameter blind bolt of the adjustable bushing fastener type that operates by radial expansion of radially expandable bushing 24. Alternatively, adjustable diameter fastener assembly 600 is any type of adjustable diameter fastener assembly, for example, and without limitation, a compression or clamp-up type fastener assembly.

In the exemplary embodiment, adjustable diameter fastener assembly 600 functions substantially similar to adjustable diameter fastener assembly 400, but includes a smooth head portion 610 rather than the hexagonal head portion 414 (shown in FIG. 15) of threaded member 408 (shown in FIG. 15). In particular, lock washer 604 is fabricated substantially similar to lock washer 404 (shown in FIG. 15), lock member 606 is fabricated substantially similar to lock member 406 (shown in FIG. 15), and lock nut 608 is fabricated substantially similar to lock nut 412 (shown in FIG. 15). As such, the rotational fixing of lock nut 608 is substantially the same as described above for adjustable diameter fastener assembly 400, with respect to FIGS. 16 and 17.

Figure 30:
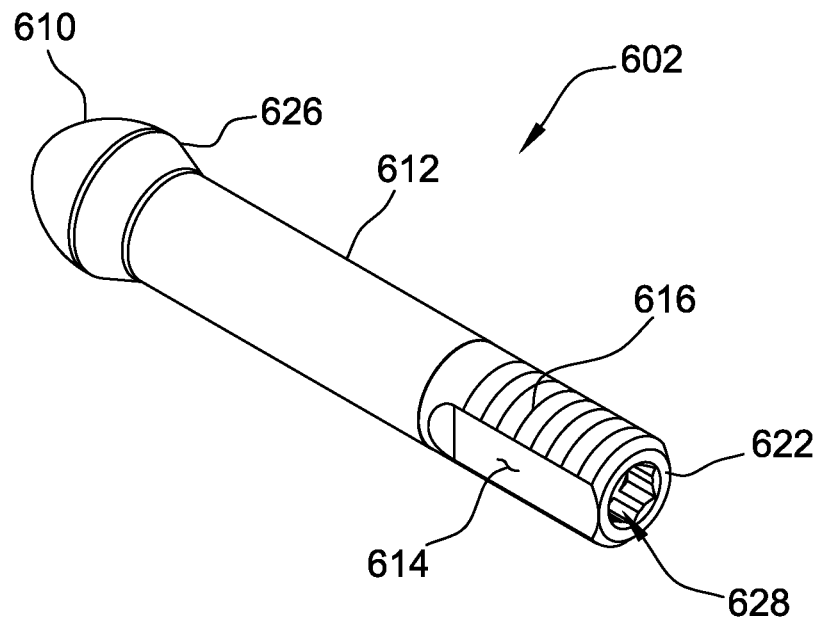
FIG. 30 is a perspective view of a threaded member of the adjustable diameter fastener assembly shown in FIG. 29.
Figure 31:
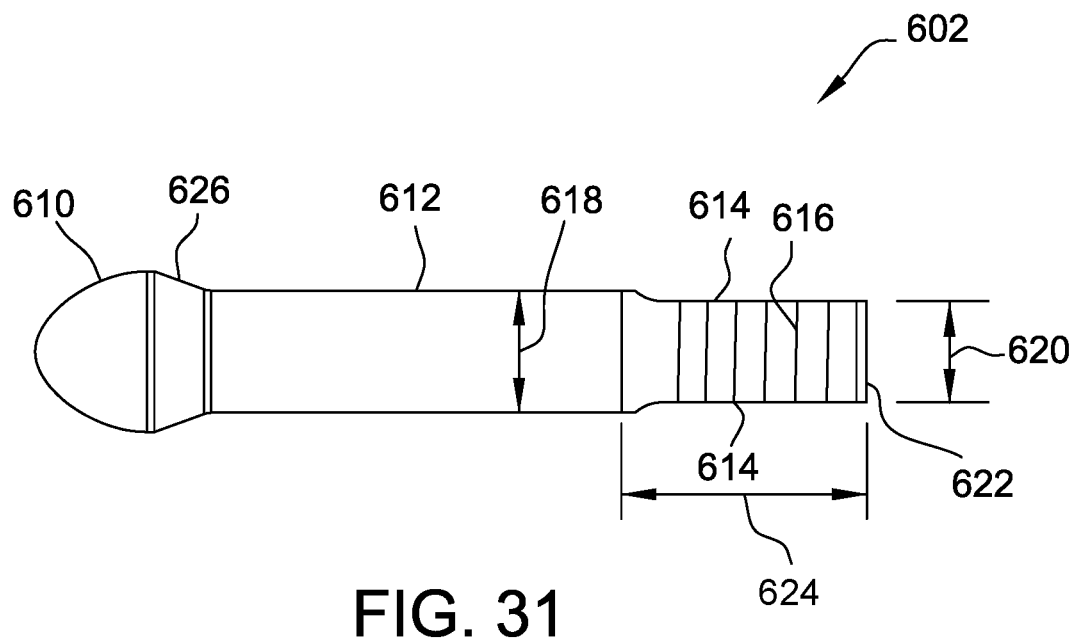
FIG. 31 is a side view of the threaded member shown in FIG. 30.

FIG. 30 is a perspective view of threaded member 602, and FIG. 31 is a side view of threaded member 602. In the exemplary embodiment, threaded member 602 includes a smooth head portion 610, an elongated body portion 612 extending axially from head portion 610, and at least one anti-rotation feature 614. Anti-rotation feature 614 is formed substantially similar to anti-rotation feature 418 (shown in FIG. 18) and includes a pair of opposing longitudinally extending sections formed in a threaded portion 616 of body portion 612. It is contemplated that anti-rotation feature 614 includes, for example, and without limitation, flats, notches, grooves, and/or any other feature that enables threaded member 602 to function as described herein. Body portion 612 has a diameter 618 defining a size of threaded member 602. Anti-rotation feature 614 includes a pair of flat portions that are parallel to each other and are spaced apart a width 620 which is smaller than diameter 618. Anti-rotation features 614 are substantially equal in size and shape, and extend along at least a portion of threaded portion 616 of body portion 612 from an end 622 of threaded member 602 a predefined length 624. It is contemplated that anti-rotation features 614 can extend any length 624 along body portion 612, up to and including extending to head portion 610.

In the exemplary embodiment, as shown in FIG. 29, head portion 610 is a curved or rounded head having a width substantially similar to a width or diameter of bushing 24. Alternatively, head portion 610 is any shape or form that enables adjustable diameter fastener assembly 600 to function as described herein. Head portion 610 includes a wedge portion 626 configured to receive a portion of bushing 24 (shown in FIG. 29) to facilitate compression of bushing 24 during use of adjustable diameter fastener assembly 600.

In the exemplary embodiment, as shown in FIG. 30, end 622 of threaded member 602 includes a socket 628 formed in body portion 612. Socket 628 is formed as a hexagonal socket to facilitate receiving a tool used to secure threaded member 602 against rotation while lock nut 608 is tightened and/or loosened. Alternatively, socket 628 is any shape or form, for example, and without limitation, a spline head and/or a slot, that enables adjustable diameter fastener assembly 600 to function as described herein.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

The fastening device technology described herein has unlimited application in industry and other uses. Particularly advantageous applications will involve use near motors or moving equipment in which vibration may cause loosening of traditional fasteners such as in automotive applications, aerospace applications, oil and gas, and manufacturing machinery. The present fastening device technology is also well suited for medical applications such as attaching pedicle screws to spinal rods, attaching spinal plates and fracture plates, fixing artificial joints, like hips and knees, orthopedic and maxillofacial external fixator systems, and the like. In particular, those skilled in the art will readily appreciate that embodiments of the fastening device technology described herein can withstand high temperature applications, for example, they can withstand temperatures as high as the material they are fabricated from can tolerate, and are easily applied, removed and reused. In addition, it is contemplated that the tightening of a nut number on a bolt member can be blind. For example, instead of the head portions, flats defined on the bolt member can be held or otherwise fixed during tightening.

In addition, some embodiments described herein provide adjustable diameter locking and vibration resistant fastener assemblies. For example, as described in the embodiments herein, when a tool is removed from the associated fastener assembly, teeth on the lock member engage the notches of the respective lock washer. When the teeth are engaged, the lock nut is rotationally locked due to the rotational locking relationship of the lock washer to the lock member. When the tool is applied to the lock nut, the lock member is displaced radially inward to disengage the teeth from the notches. When the teeth are disengaged from the lock washer notches, the lock nut is rotationally free relative to the lock washer and the fitting body.

Exemplary embodiments of systems and methods for rotationally locked adjustable diameter fastener assemblies are described above. The systems and methods are not limited to the specific embodiments described herein, but rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A locking mechanism for a fastener, said locking mechanism comprising:
   a lock nut;
   a lock member releasably coupled to said lock nut for rotation therewith, said lock member comprising an annular body comprising a radially-extending detent member; and
   a lock washer comprising an axially-extending wall about a periphery of said lock washer, said axially-extending wall defining an inner cavity for receiving a portion of said annular body of said lock member therein and comprising a plurality of radially-extending notches defined therein and configured to receive said radially-extending detent member, wherein said locking mechanism is positionable in an unlocked configuration in which said lock member and said lock nut are rotatable relative to said lock washer when said annular body is positioned within the inner cavity of said lock washer.

2. A locking mechanism in accordance with claim 1, wherein said lock nut further comprises a peripheral surface comprising an axially-extending slot defined therein.

3. A locking mechanism in accordance with claim 1, wherein said annular body is positionable between a locked configuration in which said radially-extending detent member is in a radially outward position, and the unlocked configuration in which said radially-extending detent member is in a radially inward position.

4. A locking mechanism in accordance with claim 1, wherein said lock member further comprises an axially-extending spring finger coupled to said annular body, said axially-extending spring finger comprising a free end that extends radially inward relative to said annular body and engages said lock nut.

5. A locking mechanism in accordance with claim 4, wherein said axially-extending spring finger comprises a plurality of axially-extending spring fingers.

6. A locking mechanism for a fastener, said locking mechanism comprising:
   a lock nut, wherein said lock nut further comprises an axially-extending slot defined therein;
   a lock member releasably coupled to said lock nut for rotation therewith, said lock member comprising an annular body comprising a radially-extending detent member, wherein said lock member further comprises an axially-extending spring finger coupled to said annular body, said axially-extending spring finger comprising a free end that extends radially inward relative to said annular body and engages said lock nut; and
   a lock washer comprising an axially-extending wall about a periphery of said lock washer, said axially-extending wall defining an inner cavity for receiving a portion of said annular body of said lock member therein and comprising a plurality of radially-extending notches defined therein and configured to receive said radially-extending detent member, said locking mechanism positionable in a locked configuration in which said axially-extending spring finger at least partially engages said axially-extending slot, said radially-extending detent member engaging a radially-extending notch of said plurality of radially-extending notches such that said lock nut is rotationally fixed relative to said lock washer.

7. An adjustable diameter fastener assembly comprising:
   a threaded member defining a longitudinal axis and comprising a body portion and at least one anti-rotation feature formed in said body portion;
   a radially expandable bushing slidably coupled about said threaded member;
   a lock nut configured to threadably engage said threaded member, said lock nut comprising a peripheral surface comprising an axially-extending slot defined therein;
   a lock member releasably coupled to said lock nut, said lock member comprising an annular body and an axially-extending spring finger coupled to said annular body, said axially-extending spring finger comprising a free end that extends radially inward relative to said annular body, said annular body comprising a radially-extending detent member; and
   a lock washer comprising an axially-extending wall about a periphery of said lock washer, said axially-extending wall defining an inner cavity for receiving a portion of said annular body of said lock member therein and comprising a plurality of radially-extending notches defined therein, wherein each radially-extending notch of said plurality of radially-extending notches is configured to receive said radially-extending detent member.

8. An adjustable diameter fastener in accordance with claim 7, wherein said lock washer further comprises a central portion comprising an aperture extending therethrough, said central portion comprising at least one anti-rotation structure configured to engage said at least one anti-rotation feature of said threaded member and rotationally fix said lock washer with respect to said threaded member.

9. An adjustable diameter fastener in accordance with claim 7, wherein said body portion has a diameter, said at least one anti-rotation feature comprising a pair of opposing flat sections spaced apart a predetermined distance that is smaller than the diameter of said body portion.

10. An adjustable diameter fastener in accordance with claim 9, wherein said lock washer further comprises a central portion comprising an aperture extending therethrough, said aperture comprising a diameter greater than the diameter of said body portion.

11. An adjustable diameter fastener in accordance with claim 7, wherein said fastener assembly is positionable in a locked configuration in which said axially-extending spring finger at least partially engages said axially-extending slot, and said radially-extending detent member engages a radially-extending notch of said plurality of radially-extending notches such that said lock nut is rotationally fixed relative to said lock washer.

12. An adjustable diameter fastener in accordance with claim 7, wherein said fastener assembly is positionable in an unlocked configuration in which said axially-extending spring finger is displaced radially inward of said peripheral surface and positioned in said axially-extending slot such that said radially-extending detent member is displaced radially inward relative to said plurality of radially-extending notches, and said radially-extending detent member is disengaged from said plurality of radially-extending notches such that said lock nut is rotatable relative to said lock washer.

13. An adjustable diameter fastener in accordance with claim 7, wherein said body portion comprises a first threaded portion at a first end of said threaded member, and a second threaded portion at a second end of said threaded member.

14. An adjustable diameter fastener in accordance with claim 13, wherein said at least one anti-rotation feature comprises a first anti-rotation feature formed in at least a portion of said first threaded portion, and a second anti-rotation feature formed in at least a portion of said second threaded portion.

15. An adjustable diameter fastener in accordance with claim 7, wherein said threaded member further comprises a head portion coupled to an end of said body portion.

16. An adjustable diameter fastener in accordance with claim 15, wherein said head portion comprises one of the following: a hexagonal head, a spline head, a flat head, a socket cap head, a tulip head, and a pan head.

17. An adjustable diameter fastener in accordance with claim 15, wherein said head portion comprises a curved head portion comprising a width substantially similar to a width of said radially expandable bushing.

18. An adjustable diameter fastener in accordance with claim 7, wherein said threaded member further comprises a socket formed in an end of said body portion.

19. An adjustable diameter fastener in accordance with claim 7, wherein said axially-extending spring finger comprises a plurality of axially-extending spring fingers.

20. An adjustable diameter fastener in accordance with claim 7, wherein said lock nut further comprises a head portion, a shoulder portion extending axially from said head portion, and a threaded portion extending axially from said shoulder portion, said head portion defining said peripheral surface, said shoulder portion configured to receive said annular body thereabout and to extend into said inner cavity of said lock washer.

* * * * *